(12) United States Patent
Shmayahu et al.

(10) Patent No.: US 11,793,571 B2
(45) Date of Patent: *Oct. 24, 2023

(54) REAL-TIME DISPLAY OF TREATMENT-RELATED TISSUE CHANGES USING VIRTUAL MATERIAL

(71) Applicant: Navix International Limited, Road Town (VG)

(72) Inventors: Yizhaq Shmayahu, Ramat-HaSharon (IL); Yitzhack Schwartz, Haifa (IL)

(73) Assignee: Navix International Limited, Road Town (VG)

( * ) Notice: Subject to any disclaimer, the term of this patent is extended or adjusted under 35 U.S.C. 154(b) by 455 days.

This patent is subject to a terminal disclaimer.

(21) Appl. No.: 16/906,041

(22) Filed: Jun. 19, 2020

(65) Prior Publication Data
US 2020/0315709 A1 Oct. 8, 2020

Related U.S. Application Data

(63) Continuation of application No. 16/349,648, filed as application No. PCT/IB2017/057176 on Nov. 16, 2017, now Pat. No. 10,709,507.
(Continued)

(51) Int. Cl.
*A61B 34/10* (2016.01)
*A61B 90/00* (2016.01)
(Continued)

(52) U.S. Cl.
CPC .............. *A61B 34/10* (2016.02); *A61B 18/06* (2013.01); *A61B 18/1492* (2013.01);
(Continued)

(58) Field of Classification Search
USPC ....................................................... 382/128
See application file for complete search history.

(56) References Cited

U.S. PATENT DOCUMENTS

| 4,917,097 A | 4/1990 | Proudian et al. |
| 5,598,848 A | 2/1997 | Swanson et al. |

(Continued)

FOREIGN PATENT DOCUMENTS

| EP | 2248480 | 11/2010 |
| HR | P20131208 | 3/2014 |

(Continued)

OTHER PUBLICATIONS

Official Action dated May 12, 2021 from the U.S. Appl. No. 16/349,646. (46 pages).

(Continued)

*Primary Examiner* — Ishrat I Sherali

(57) ABSTRACT

In some embodiments, data sensed and/or operational parameters used during a catheterization procedure are used in the motion frame-rate updating and visual rendering of a simulated organ geometry. The organ geometry is rendered as a virtual material using a software environment (preferably a graphical game engine) which applies simulated optical laws to material appearance parameters affecting the virtual material's visual appearance, as part of simulating a scene comprising the simulated organ geometry, and optionally also comprising simulated views of a catheter probe used for sensing and/or treatment. Optionally, measurements of and/or effects on tissue by sensing and/or commanded probe-tissue interactions are converted into material appearance changes, allowing dynamic visual simulation of intra-body states and/or events based on optionally non-visual input data. In some embodiments, physiology, motion physics, and/or other physical processes are simulated based on live inputs as part of associating material appearance properties to the simulated tissue's geometry.

29 Claims, 11 Drawing Sheets

Related U.S. Application Data

(60) Provisional application No. 62/422,713, filed on Nov. 16, 2016, provisional application No. 62/422,705, filed on Nov. 16, 2016, provisional application No. 62/422,708, filed on Nov. 16, 2016.

(51) Int. Cl.
- A61B 18/06 (2006.01)
- A61B 18/14 (2006.01)
- A61B 18/24 (2006.01)
- A61M 25/01 (2006.01)
- A61B 17/32 (2006.01)
- A61B 18/00 (2006.01)
- A61B 18/02 (2006.01)
- A61B 18/18 (2006.01)

(52) U.S. Cl.
CPC .............. *A61B 18/24* (2013.01); *A61B 90/37* (2016.02); *A61M 25/0105* (2013.01); A61B 2017/320069 (2017.08); A61B 2018/00285 (2013.01); A61B 2018/00577 (2013.01); A61B 2018/00613 (2013.01); A61B 2018/0212 (2013.01); A61B 2018/1861 (2013.01); A61B 2034/104 (2016.02); A61B 2034/105 (2016.02); A61M 2025/0166 (2013.01); A61M 2202/049 (2013.01); A61M 2202/0484 (2013.01); A61M 2202/07 (2013.01); A61M 2202/09 (2013.01); A61M 2210/1053 (2013.01); A61M 2210/1071 (2013.01); A61M 2210/1082 (2013.01); A61M 2210/125 (2013.01)

(56) References Cited

U.S. PATENT DOCUMENTS

| | | | |
|---|---|---|---|
| 5,724,978 A | 3/1998 | Tenhoff | |
| 6,019,725 A | 2/2000 | Vesely et al. | |
| 6,038,468 A | 3/2000 | Rex | |
| 6,301,496 B1* | 10/2001 | Reisfeld | A61B 5/341 |
| | | | 600/407 |
| 6,317,621 B1 | 11/2001 | Graumann et al. | |
| 6,515,657 B1 | 2/2003 | Zanelli | |
| 6,989,010 B2 | 1/2006 | Francischelli et al. | |
| 7,001,383 B2 | 2/2006 | Keidar | |
| 7,146,210 B2 | 12/2006 | Palti | |
| 7,306,593 B2* | 12/2007 | Keidar | A61B 90/92 |
| | | | 606/41 |
| 8,160,690 B2 | 4/2012 | Wilfley et al. | |
| 8,401,616 B2* | 3/2013 | Verard | A61B 8/4254 |
| | | | 600/407 |
| 8,403,925 B2 | 3/2013 | Miller et al. | |
| 8,454,589 B2 | 6/2013 | Deno et al. | |
| 8,556,888 B2 | 10/2013 | Nields et al. | |
| 8,565,860 B2* | 10/2013 | Kimchy | A61B 6/037 |
| | | | 250/363.01 |
| 8,909,325 B2* | 12/2014 | Kimchy | A61B 5/415 |
| | | | 600/407 |
| 9,101,333 B2* | 8/2015 | Schwartz | A61B 5/361 |
| 9,259,290 B2 | 2/2016 | Jenkins et al. | |
| 9,271,782 B2 | 3/2016 | Paul et al. | |
| 9,283,051 B2 | 3/2016 | Garcia et al. | |
| 9,636,164 B2 | 5/2017 | Panescu et al. | |
| 9,743,854 B2 | 8/2017 | Stewart et al. | |
| 9,757,191 B2 | 9/2017 | Avitall et al. | |
| 9,955,946 B2 | 5/2018 | Miller et al. | |
| 9,980,653 B2 | 5/2018 | Lichtenstein et al. | |
| 10,292,588 B2 | 5/2019 | Ben-Haim | |
| 10,709,507 B2* | 7/2020 | Shmayahu | A61M 25/0105 |
| 11,010,983 B2* | 5/2021 | Shmayahu | A61B 34/10 |
| 11,284,813 B2* | 3/2022 | Shmayahu | A61B 18/1492 |
| 2003/0074011 A1 | 4/2003 | Gilboa et al. | |
| 2004/0009459 A1* | 1/2004 | Anderson | G06T 19/00 |
| | | | 703/11 |
| 2004/0039278 A1 | 2/2004 | Wacker et al. | |
| 2004/0044279 A1 | 3/2004 | Lewin et al. | |
| 2004/0054248 A1* | 3/2004 | Kimchy | A61B 6/4057 |
| | | | 600/3 |
| 2004/0097805 A1 | 5/2004 | Verard et al. | |
| 2004/0147920 A1* | 7/2004 | Keidar | A61B 8/12 |
| | | | 606/41 |
| 2004/0176804 A1 | 9/2004 | Palti | |
| 2005/0015006 A1 | 1/2005 | Mitschke et al. | |
| 2005/0033164 A1 | 2/2005 | Yatsuo et al. | |
| 2005/0054913 A1 | 3/2005 | Duerk et al. | |
| 2005/0054918 A1 | 3/2005 | Sra | |
| 2005/0245814 A1 | 11/2005 | Anderson et al. | |
| 2006/0089552 A1 | 4/2006 | Goldbach | |
| 2007/0043296 A1 | 2/2007 | Schwartz | |
| 2007/0167706 A1 | 7/2007 | Boese et al. | |
| 2007/0167726 A1 | 7/2007 | Unal et al. | |
| 2008/0114235 A1 | 5/2008 | Unal et al. | |
| 2008/0118135 A1 | 5/2008 | Averbuch et al. | |
| 2008/0170033 A1 | 7/2008 | Schultz | |
| 2008/0183070 A1 | 7/2008 | Unal et al. | |
| 2008/0208031 A1 | 8/2008 | Kurpad et al. | |
| 2008/0221425 A1 | 9/2008 | Olson et al. | |
| 2008/0230705 A1 | 9/2008 | Rousso et al. | |
| 2008/0275465 A1 | 11/2008 | Paul et al. | |
| 2008/0281319 A1 | 11/2008 | Paul et al. | |
| 2009/0010519 A1 | 1/2009 | Wakai et al. | |
| 2009/0015818 A1 | 1/2009 | Ikeda et al. | |
| 2009/0076499 A1 | 3/2009 | Azure | |
| 2009/0148012 A1 | 6/2009 | Altmann et al. | |
| 2009/0149753 A1* | 6/2009 | Govari | A61B 18/1492 |
| | | | 600/439 |
| 2009/0275828 A1 | 11/2009 | Shachar et al. | |
| 2009/0306643 A1 | 12/2009 | Pappone et al. | |
| 2010/0063400 A1 | 3/2010 | Hall et al. | |
| 2010/0069921 A1 | 3/2010 | Miller et al. | |
| 2010/0185087 A1 | 7/2010 | Nields et al. | |
| 2010/0217116 A1 | 8/2010 | Eck et al. | |
| 2010/0249579 A1 | 9/2010 | Starks | |
| 2010/0298826 A1 | 11/2010 | Leo et al. | |
| 2010/0312094 A1 | 12/2010 | Guttman et al. | |
| 2010/0312096 A1 | 12/2010 | Guttman et al. | |
| 2010/0331694 A1 | 12/2010 | Waki | |
| 2011/0122326 A1 | 5/2011 | Jang et al. | |
| 2011/0144524 A1 | 6/2011 | Fish et al. | |
| 2011/0160569 A1* | 6/2011 | Cohen | G06T 19/00 |
| | | | 600/424 |
| 2012/0116210 A1 | 5/2012 | Zino | |
| 2012/0123250 A1 | 5/2012 | Pang et al. | |
| 2012/0172724 A1 | 7/2012 | Hill et al. | |
| 2012/0173217 A1 | 7/2012 | Heimbecher | |
| 2012/0238866 A1 | 9/2012 | Wang et al. | |
| 2013/0123773 A1* | 5/2013 | Schwartz | A61B 5/361 |
| | | | 606/34 |
| 2013/0137980 A1 | 5/2013 | Waters et al. | |
| 2014/0111639 A1 | 4/2014 | Tanaka et al. | |
| 2014/0187949 A1 | 7/2014 | Zhao et al. | |
| 2014/0243641 A1 | 8/2014 | Boveja et al. | |
| 2014/0330111 A1 | 11/2014 | Lichtenstein et al. | |
| 2015/0099942 A1 | 4/2015 | Edouard | |
| 2015/0141978 A1 | 5/2015 | Subramaniam et al. | |
| 2015/0254422 A1 | 9/2015 | Avisar | |
| 2015/0282749 A1 | 10/2015 | Zand et al. | |
| 2016/0066977 A1 | 3/2016 | Neal, II et al. | |
| 2016/0135762 A1 | 5/2016 | Mihailescu et al. | |
| 2016/0249989 A1 | 9/2016 | DeVam et al. | |
| 2017/0009805 A1 | 4/2017 | Voth | |
| 2017/0098055 A1 | 4/2017 | Voth | |
| 2017/0263021 A1* | 9/2017 | Ben-Haim | A61B 6/4258 |
| 2017/0281281 A1 | 10/2017 | He et al. | |
| 2018/0116751 A1 | 5/2018 | Schwartz et al. | |
| 2018/0125575 A1 | 5/2018 | Schwartz et al. | |
| 2018/0325597 A1 | 11/2018 | Schwartz et al. | |
| 2019/0328275 A1 | 10/2019 | Shmayahu et al. | |
| 2019/0328458 A1 | 10/2019 | Shmayahu et al. | |
| 2019/0340837 A1 | 11/2019 | Shmayahu et al. | |

(56) References Cited

U.S. PATENT DOCUMENTS

| | | | |
|---|---|---|---|
| 2020/0022649 | A1 | 1/2020 | Rodriguez et al. |
| 2020/0060757 | A1 | 2/2020 | Ben-Haim et al. |
| 2021/0241542 | A1 | 8/2021 | Shmayahu et al. |

FOREIGN PATENT DOCUMENTS

| | | |
|---|---|---|
| JP | 2001-340336 | 12/2001 |
| JP | 2005-199072 | 7/2005 |
| JP | 2009-518130 | 5/2009 |
| JP | 2014-533130 | 12/2014 |
| JP | 2015-503365 | 2/2015 |
| WO | WO 2007/067628 | 6/1997 |
| WO | WO 2007/067628 | 6/2007 |
| WO | WO 2008/104914 | 9/2008 |
| WO | WO 2010/102794 | 9/2010 |
| WO | WO 2013/052590 | 4/2013 |
| WO | WO 2013/096916 | 6/2013 |
| WO | WO 2013/192598 | 12/2013 |
| WO | WO 2016/038499 | 3/2016 |
| WO | WO 2018/092059 | 5/2018 |
| WO | WO 2018/092062 | 5/2018 |
| WO | WO 2018/092063 | 5/2018 |

OTHER PUBLICATIONS

Notice of Allowance dated Jan. 8, 2021 From the U.S. Appl. No. 16/461,384. (37 pages).
International Preliminary Report on Patentability dated May 31, 2019 From the International Bureau of WIPO Re. Application No. PCT/IB2017/057169. (9 Pages).
International Preliminary Report on Patentability dated May 31, 2019 From the International Bureau of WIPO Re. Application No. PCT/IB2017/057175. (9 Pages).
International Preliminary Report on Patentability dated May 31, 2019 From the International Bureau of WIPO Re. Application No. PCT/IB2017/057176. (10 Pages).
International Search Report and the Written Opinion dated Feb. 22, 2018 From the International Searching Authority Re. Application No. PCT/IB2017/057169. (14 Pages).
International Search Report and the Written Opinion dated Feb. 22, 2018 From the International Searching Authority Re. Application No. PCT/IB2017/057175. (15 Pages).
International Search Report and the Written Opinion dated Feb. 22, 2018 From the International Searching Authority Re. Application No. PCT/IB2017/057176. (15 Pages).
Notice of Allowance dated Mar. 9, 2020 from the U.S. Appl. No. 16/349,648. (28 pages).
Restriction Official Action dated Jun. 12, 2020 from the U.S. Appl. No. 16/461,384. (6 pages).
Official Action dated Jun. 27, 2022 from U.S. Appl. No. 17/239,743. (25 pages).
Third-Party Submission under 37 CFR 1.290 filed on Mar. 2, 2021 From the U.S. Appl. No. 16/349,646. (2 Pages).
USPTO Communication dated Mar. 5, 2021 RE Third-Party Submission from the U.S. Appl. No. 16/349,646.(2 Pages).
Communication Pursuant to Article 94(3) EPC dated Sep. 4, 2020 From the European Patent Office Re. Application No. 16725589.2. (8 Pages).
Communication Pursuant to Article 94(3) EPC dated Sep. 25, 2020 From the European Patent Office Re. Application No. 16726181.7. (5 Pages).
Decision of Refusal dated Oct. 20, 2020 From the Japan Patent Office Re. Application No. 2017-558704 and Its Translation Into English. (6 Pages).
Final Official Action dated Jul. 1, 2020 from the U.S. Appl. No. 15/570,341. (24 pages).
Final Official Action dated Jun. 22, 2020 from the U.S. Appl. No. 15/573,491. (14 pages).
International Preliminary Report on Patentability dated Jul. 25, 2019 From the International Bureau of WIPO Re. Application No. PCT/IB2018/050195. (9 Pages).
Interview Summary dated Dec. 15, 2020 from the U.S. Appl. No. 15/570,341. (4 pages).
Interview Summary dated Sep. 29, 2020 from the U.S. Appl. No. 15/573,491. (3 pages).
Notice of Allowance dated Oct. 22, 2020 From the U.S. Appl. No. 15/573,491. (6 Pages).
Notice of Allowance dated Feb. 24, 2021 From the U.S. Appl. No. 15/570,341. (8 Pages).
Notice of Allowance dated Sep. 4, 2020 from the U.S. Appl. No. 15/573,493. (14 pages).
Notice of Reasons for Refusal dated Mar. 3, 2020 From the Japan Patent Office Re. Application No. 2017-558704 and Its Translation Into English. (14 Pages).
Notice of Reasons for Refusal dated Apr. 21, 2020 From the Japan Patent Office Re. Application No. 2017-558702 and Its Translation Into English. (16 Pages).
Official Action dated Mar. 5, 2020 From the U.S. Appl. No. 15/573,493. (21 pages).
Official Action dated Feb. 6, 2020 From the U.S. Appl. No. 15/570,341. (33 pages).
Official Action dated Jan. 8, 2020 From the U.S. Appl. No. 15/573,491. (20 pages).
Restriction Official Action dated Nov. 19, 2019 From the U.S. Appl. No. 15/573,493. (6 pages).
Koruth et al. "Tissue Temperature Sensing During Irrigated Radiofrequency Ablation: A Novel Strategy to Predict Steam Pops", Heart Rhythm, 33rd Annual Scientific Sessions, Boston, MA, USA, May 9-12, 2012, Presentation Abstract, # AB12-02, May 10, 2012.
Sulkin et al. "Novel Measure of Local Impedance Predicts Catheter-Tissue Contact and Lesion Formation", Circulation: Arrhythmia and Electrophysiology, 11(4): e005831-1-e005831-21, Apr. 2018.
Notice of Allowance dated Feb. 16, 2023 from the U.S. Appl. No. 17/239,743. (6 pages).

\* cited by examiner

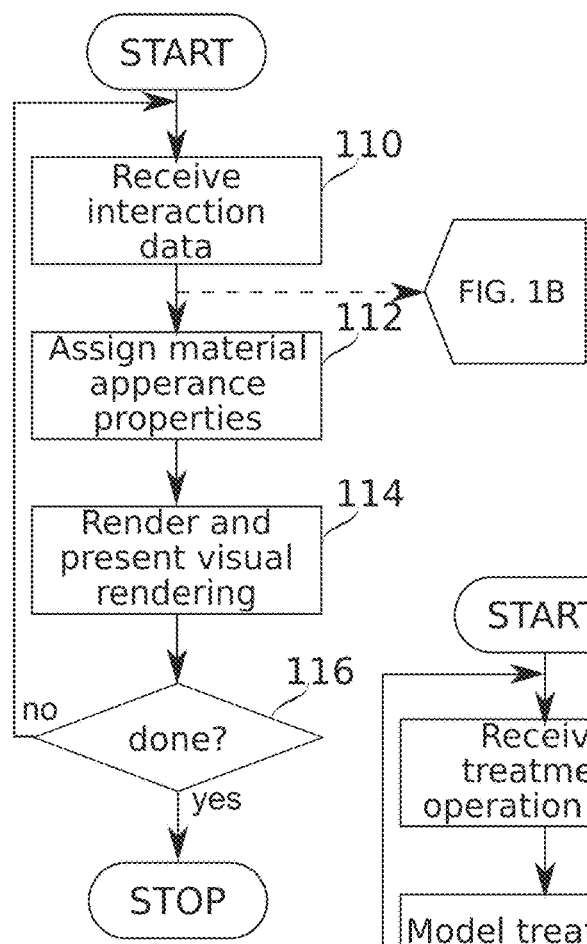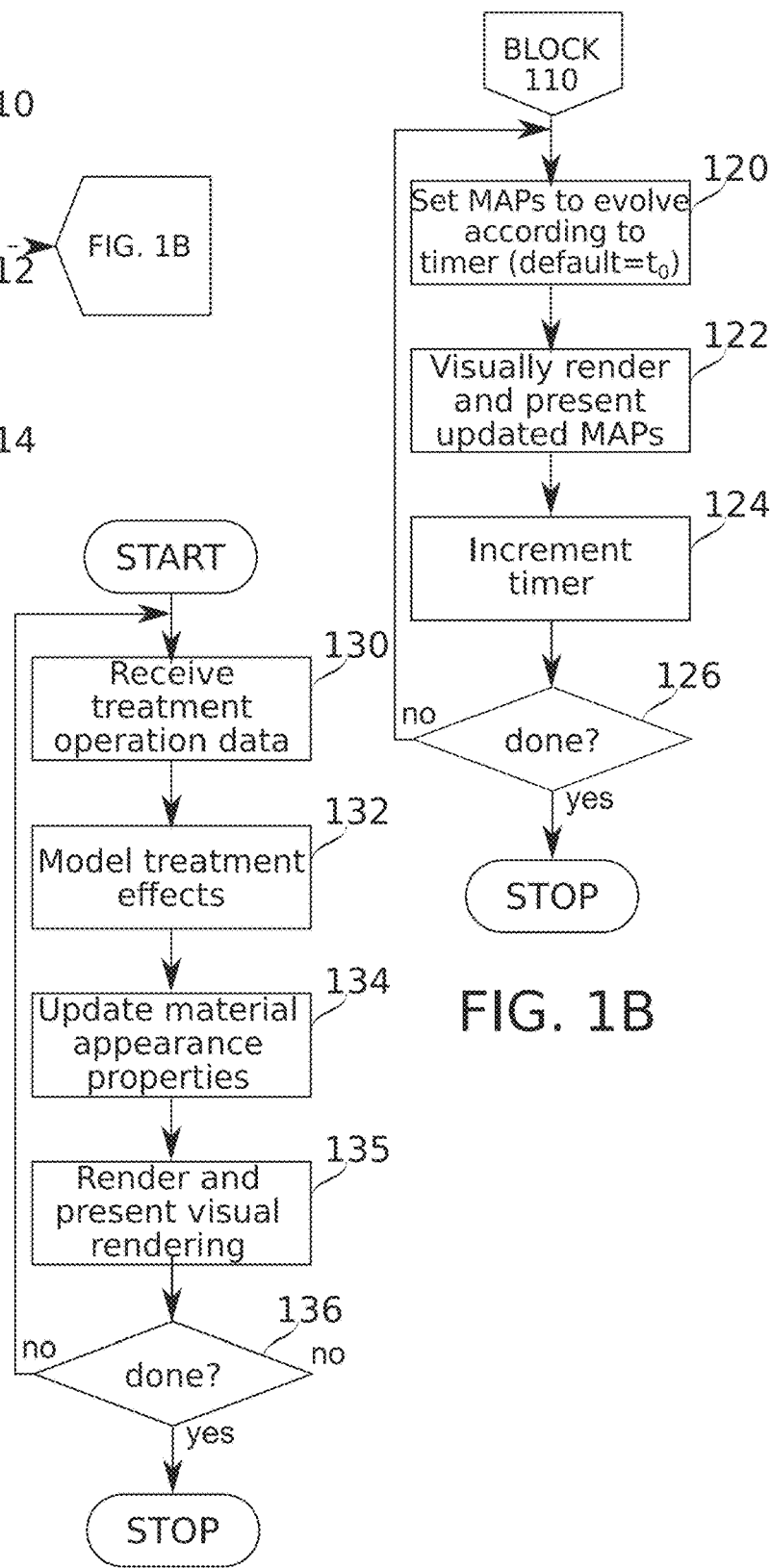

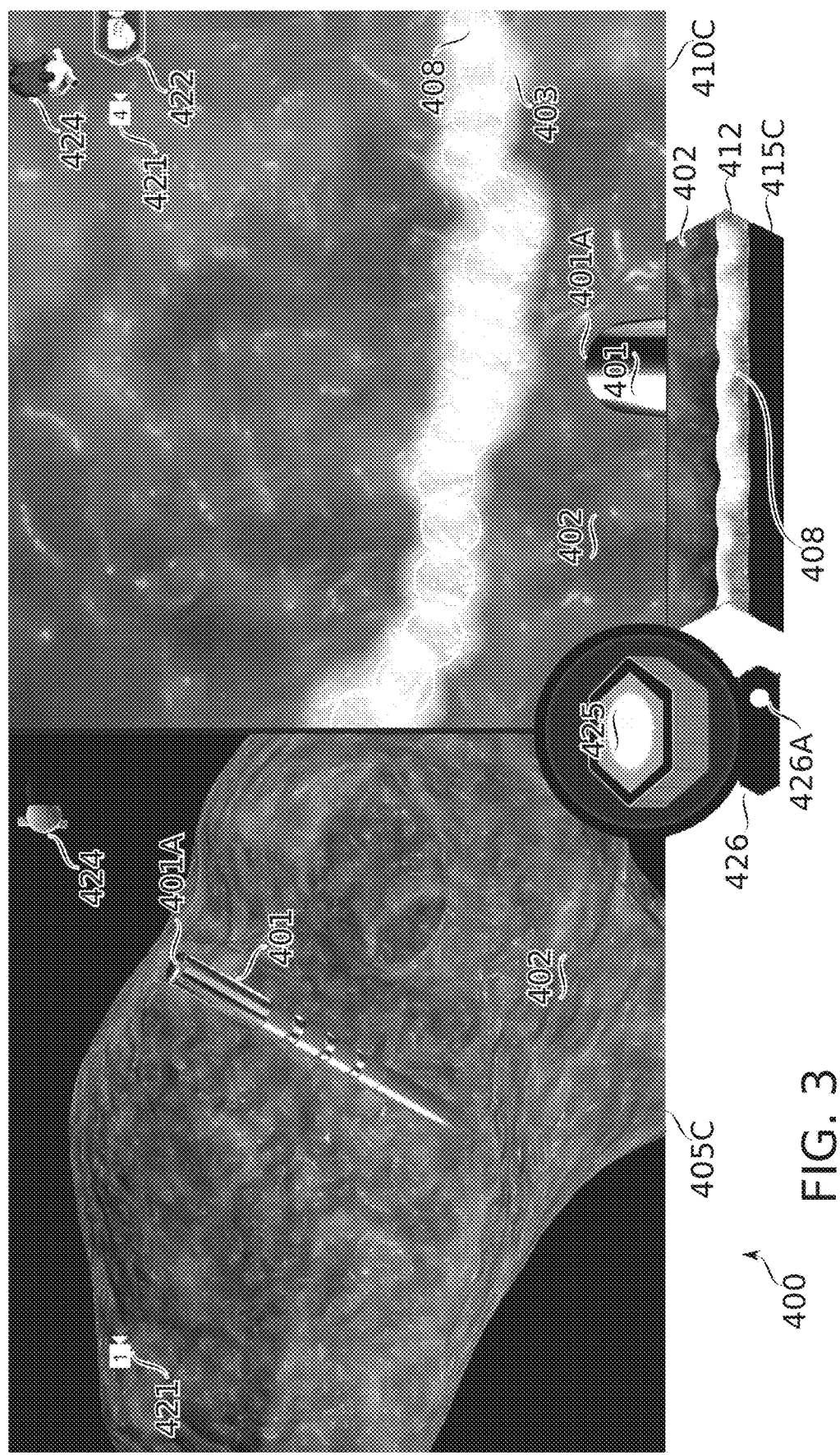

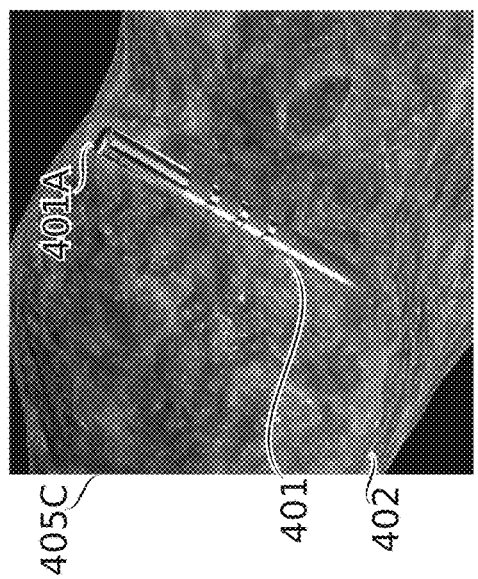
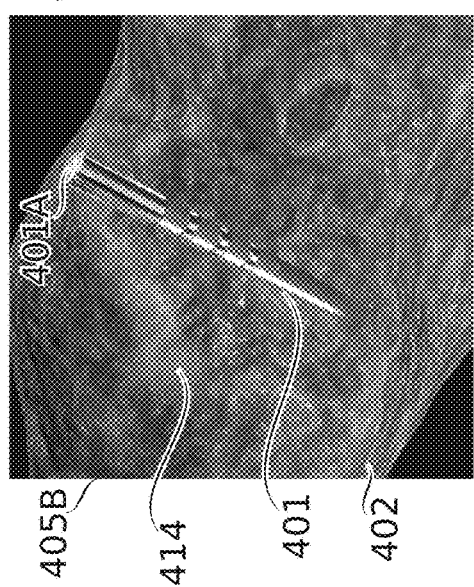
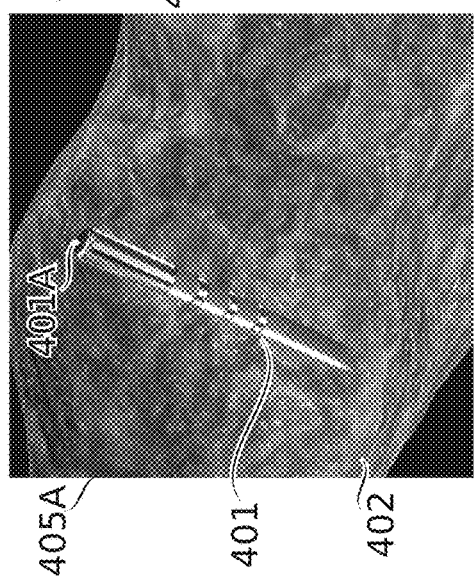
FIG. 4A
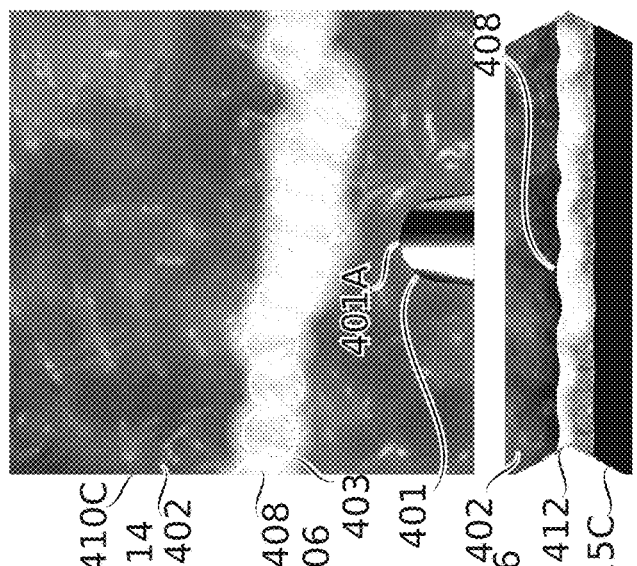
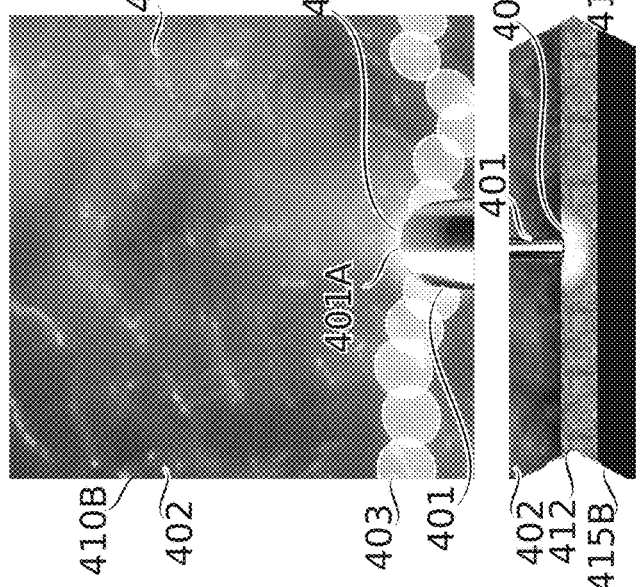
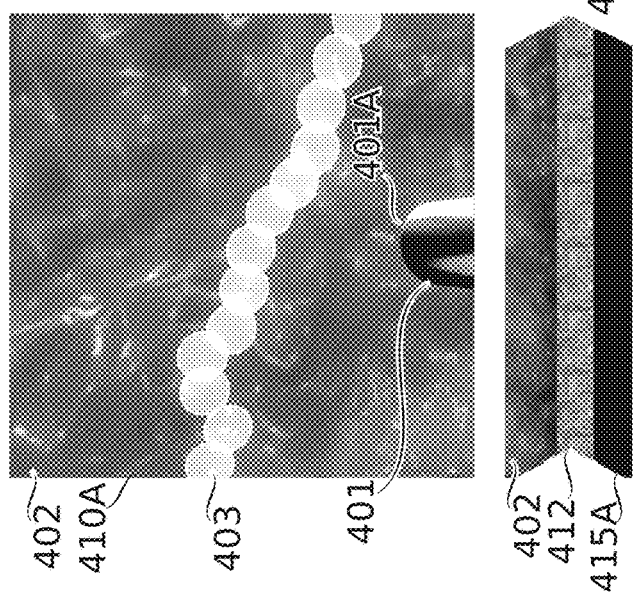
FIG. 4B
FIG. 4C

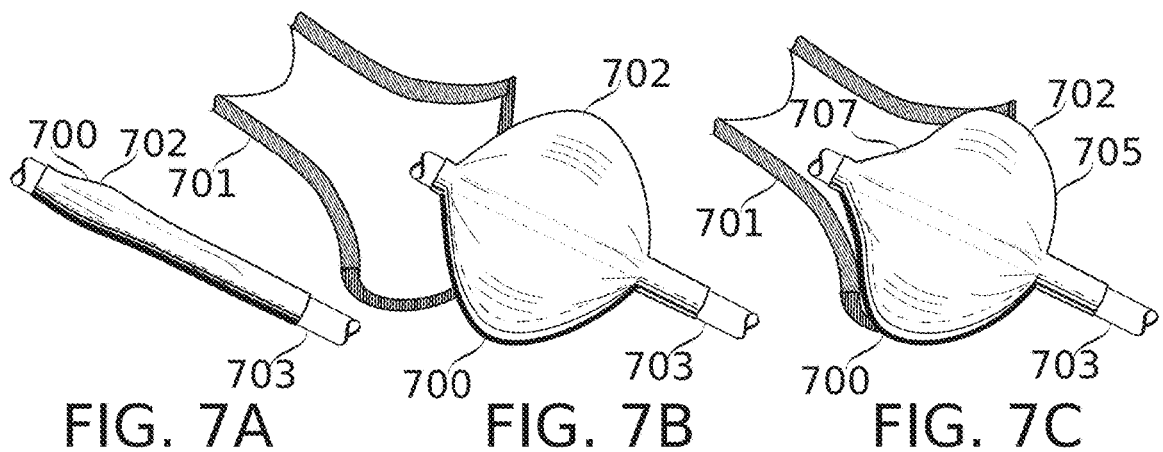
FIG. 7A  FIG. 7B  FIG. 7C
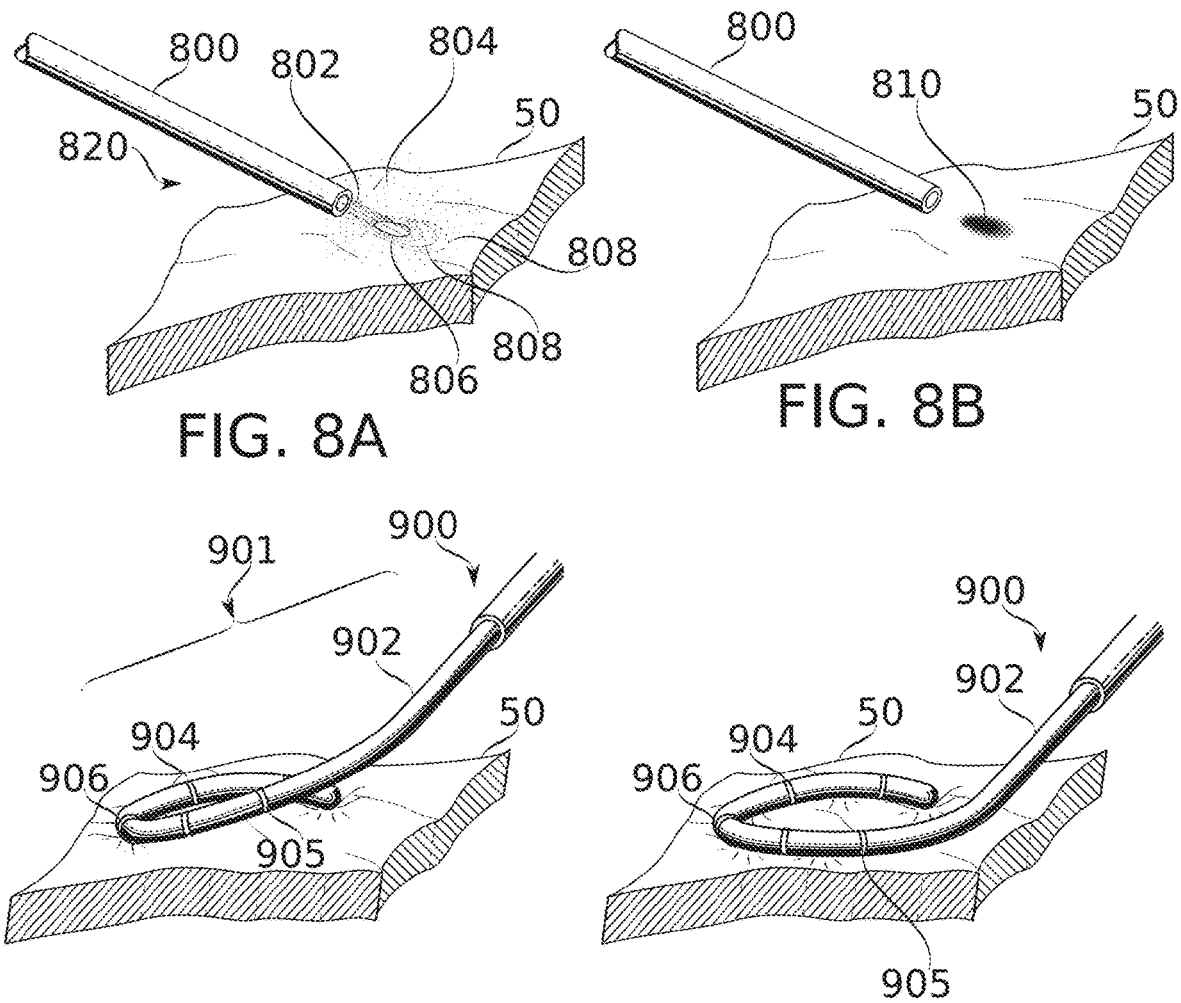
FIG. 8A  FIG. 8B
FIG. 9A  FIG. 9B

REAL-TIME DISPLAY OF TREATMENT-RELATED TISSUE CHANGES USING VIRTUAL MATERIAL

RELATED APPLICATIONS

This application is a continuation of U.S. patent application Ser. No. 16/349,648 filed on May 14, 2019, which is a National Phase of PCT Patent Application No. PCT/IB2017/057176 having International Filing Date of Nov. 16, 2017, which claims the benefit of priority under 35 USC § 119(e) of U.S. Provisional Patent Application Nos. 62/422,713, 62/422,705, 62/422,708, all filed on Nov. 16, 2016. The contents of the above applications are all incorporated by reference as if fully set forth herein in their entirety.

FIELD AND BACKGROUND OF THE INVENTION

The present invention, in some embodiments thereof, relates to the field of medical procedures using intrabody probes navigable within intrabody spaces, and more particularly, to presentation of procedure data dynamically acquired during the course of a catheter procedure.

Graphical game engines currently available comprise suites of software-implemented capabilities supporting the dynamic display and updating of simulated three-dimensional scenes. Typically, game engines include API calls supporting the creation and modification of a variety of scene objects (chiefly terrain, various types of physical objects, camera viewpoints, and lighting), a visual rendering pipeline, and optionally further services assisting tasks such as coding, animating, and/or debugging. User inputs are accepted from various user interface devices (including pointer devices, keyboards, game controllers, motion sensors, touch screens, and the like) and converted into events in the simulated environment. Well-known game engines include the Unreal® and Unity® graphical game engines (www(dot)unrealengine(dot)com; unity3d(dot)com). The rendering pipelines of modern game engines typically include facilities for creating realistic-looking visualizations of scene elements, based on properties assigned to instantiations of data objects representing those scene elements.

Several medical procedures in cardiology and other medical fields comprise the use of catheters to reach tissue targeted for diagnosis and/or treatment while minimizing procedure invasiveness. Early imaging-based techniques (such as fluoroscopy) for navigation of the catheter and monitoring of treatments continue to be refined, and are now joined by techniques such as electromagnetic field measurement-guided position sensing systems. Refinements to techniques for registration of previously imaged (for example, by CT and/or MRI) anatomical features of a patient to electromagnetic field-sensed catheter position are a subject of ongoing research and development, for example as described in International Patent Application No. IB2016/052687 to Schwartz et al. filed May 11, 2016; and International Patent Application No. IB2016/052692 to Schwartz et al. filed May 11, 2016. Intrabody sensing from catheter probes to determine information about, for example, tissue contact and/or lesion assessment, has also been described (e.g., International Patent Application No. PCT IB2016/052690 to Schwartz et al. filed May 11, 2016; and International Patent Application No. IB2016/052686 to Schwartz et al. filed May 11, 2016).

SUMMARY OF THE INVENTION

There is provided, in accordance with some embodiments of the present disclosure, a method of visually displaying tissue-probe interactions in a medical procedure, comprising: receiving interaction data indicating interactions between an intrabody probe and a body tissue region, wherein the interaction data are associated to positions within the tissue region; associating, based on the interaction data, material appearance properties to an extent of geometrical rendering data, wherein the geometrical rendering data indicate geometry of the tissue region; rendering the geometrical rendering data to a rendered image using the associated material appearance properties; and presenting the rendered image on a display.

In some embodiments, the rendering is to a rendered image from a simulated viewpoint inside a lumen of the tissue region.

In some embodiments, the rendering is to a rendered image as if lit from within a lumen of the tissue region.

In some embodiments, the associated material appearance properties indicate treatment effects on the tissue region as a result of treatment-delivering interactions between the intrabody probe and the body tissue region.

In some embodiments, the associated material appearance properties are calculated based on operational parameters according to which the treatment-delivering interactions between the intrabody probe and the body tissue region are performed.

In some embodiments, the associated material appearance properties are calculated based on measured effects of the treatment-delivering interactions between the intrabody probe and the body tissue region.

In some embodiments, the treatment-delivering interaction comprises tissue ablation.

In some embodiments, the associating comprises compositing: material appearance properties indicating effects of the interactions between the intrabody probe and the body tissue region with material appearance properties providing a visual texture indicative of the tissue structure of which the body tissue region is comprised.

In some embodiments, the interaction data includes probe-sensed characteristics of tissue in the vicinity of the intrabody probe.

In some embodiments, the intrabody probe is a catheter probe.

In some embodiments, the interaction data includes operation data indicating activation of the intrabody probe to treat tissue.

In some embodiments, the interaction data indicate a change of the tissue due to the interaction between the intrabody probe and the body tissue region.

In some embodiments, the geometrical rendering data represent thickness of a tissue in the tissue region, and the associating associates the material appearance properties across an extent of the thickness.

In some embodiments, the associating material appearance properties is as a function of time relative to a time of occurrence of the interactions.

In some embodiments, the associated is updated at a rate of every three seconds or more often.

In some embodiments, the receiving, the associating, the rendering, and the presenting are performed iteratively for a sequence of interactions between the intrabody probe and one or more body tissue regions.

In some embodiments, the rendering and the presenting are iteratively updated at a frame rate of 10 frames per second or more.

In some embodiments, the rendering is to a rendered image including a simulated view of the intrabody probe.

In some embodiments, the rendering is to a rendered image from a simulated viewpoint at least partially based on a determined position of the intrabody probe relative to the tissue region determined from measurements.

In some embodiments, the simulated viewpoint is at least partially based on a determined orientation of the intrabody probe.

In some embodiments, the rendering comprises adjusting a representation of the intrabody probe in the rendered image, based on the interaction data.

In some embodiments, the adjusting adjusts the appearance of the intrabody probe representation to a deformed shape, based on contact with a surface of the tissue region.

In some embodiments, the adjusting comprises geometrical deformation of a representation of a balloon element of the intrabody probe in the rendered image.

In some embodiments, the adjusting comprises bending of a representation of a flexible rod element of the intrabody probe.

In some embodiments, the interaction data are received from a plurality of sensors on the intrabody probe.

In some embodiments, the interactions are between a plurality of intrabody probes in simultaneous use, and a body tissue region.

In some embodiments, the receiving comprises receiving interaction data including operation data indicative of use of an ablation device operated using the intrabody probe to ablate in the body tissue region.

In some embodiments, the associating comprises updating material appearance properties based on cumulative operation of the ablation device.

In some embodiments, the associating comprises updating material appearance properties to indicate in the rendered image increasing extent of lesioning effect, based on the cumulative operation of the ablation device.

In some embodiments, the associating comprises updating material appearance properties that indicate increasing local intensity of lesioning effect, wherein the updating is based on the cumulative operation of the ablation device.

In some embodiments, the updating based on the cumulative operation of the ablation device comprises simulation of thermal effects of the ablation device on the body tissue region.

In some embodiments, the ablation device provides at least one ablation modality of the group consisting of: radio frequency ablation, cryoablation, microwave ablation, laser ablation, irreversible electroporation, substance injection ablation, and high-intensity focused ultrasound ablation.

In some embodiments, at least some material appearance properties associated by the associating are selected so that a tissue representation in the rendered image has an appearance of ablated tissue, wherein the appearance of ablated tissue comprises a difference in ablated tissue appearance compared to healthy tissue appearance in at least one of the group consisting of reflectance, absorption, scattering, specular reflection, translucency, and texture.

In some embodiments, the associating comprises associating material appearance properties as a function of time since the operation of the ablation device, to indicate gradual development of a state of the body tissue region as a result of ablation.

In some embodiments, the gradually developed state is a state of edema.

In some embodiments, the method comprises adjusting the geometrical appearance of the body tissue region to define a more swollen shape in the rendered image, to an extent based on the indicated development of the state of edema.

In some embodiments, the receiving comprises receiving interaction data indicating a force of contact between the intrabody probe and the body tissue region.

In some embodiments, the interaction data indicate a quality of contact between the intrabody probe and the body tissue region.

In some embodiments, the material appearance properties associated by the associating to the geometrical rendering data are selected, based on the contact indicated by the interaction data, for a region corresponding to a region of contact between the intrabody probe and the body tissue region.

In some embodiments, the method comprises deforming the geometrical rendering data at the region corresponding to the region of contact to an extent based on the interaction data.

In some embodiments, the interaction data indicate injection of a substance from the intrabody probe to the body tissue region.

In some embodiments, the associating comprises associating material appearance properties indicating distribution of injected substance with portions of the geometrical rendering data corresponding to portions of the body tissue region to which the injected substance is distributed.

In some embodiments, the distribution of the injected substance is determined based on modeling of the rate of spread of the injected substance through the body tissue region.

In some embodiments, the injected substance comprises a material comprising at least one from among the group consisting of ethyl alcohol, Botox®, biological cellular material, and growth factor.

In some embodiments, the body tissue region comprises a lumenal surface of an organ, and the rendered image includes a representation of the lumenal surface.

In some embodiments, the body tissue region comprises an outer surface of an organ, and the rendered image includes a representation of the outer surface.

In some embodiments, the body tissue region comprises tissue of at least one organ of the group consisting of the heart, vasculature, stomach, intestines, liver and kidney, and the rendered image includes a representation of the at least one organ.

In some embodiments, the rendered image comprises a cross-sectional view representing the body tissue region.

In some embodiments, the associating comprises associating material appearance properties to the geometrical rendering data at positions of the cross-sectional view, based on the interaction data.

In some embodiments, the associating comprises associating material appearance properties to the geometrical rendering data at positions of the cross-sectional view, based on cumulative operation of an ablation device.

In some embodiments, a surface exposed at the cross-sectional view represents a non-planar section extending through a thickness of the body tissue region.

In some embodiments, the rendered image represents the non-planar surface as a flattened surface.

In some embodiments, the rendered image represents both the cross-sectional view of the body tissue region, and a surface of an organ of the body tissue region.

There is provided, in accordance with some embodiments of the present disclosure, a method of visually displaying tissue-probe interactions, the method comprising: receiving interaction data indicating contact between an intrabody probe and a body tissue region, wherein the interaction data are associated to positions within the body tissue region; deforming geometrical rendering data indicating geometry of the tissue region, based on a change in shape of the body tissue region indicated in the interaction data; rendering the deformed geometrical rendering data to a rendered image; and presenting the rendered image.

In some embodiments, the method further comprises associating material appearance properties to an extent of the geometrical rendering data, based on the interaction data; and wherein the rendering of the deformed geometrical rendering data uses the associated material appearance properties to produce the rendered image.

In some embodiments, the rendering uses the associated material appearance properties to simulate interactions of tissue represented by the geometrical rendering data with light.

In some embodiments, the rendered image includes a cross-sectional view of the body tissue region.

In some embodiments, the extent and depth of the deforming represent a local indentation of a thickness of the body tissue region where it is intersected by the cross-sectional view.

In some embodiments, the extent and degree of the deforming simulate stretching of the body tissue region.

There is provided, in accordance with some embodiments of the present disclosure, a system for displaying effects of interactions between an intrabody probe and a body tissue region as images, the system comprising: computer circuitry configured to: receive interaction data indicating the interactions, and associated to positions within the body tissue region, associate, based on the interaction data, material appearance properties to an extent of geometrical rendering data indicating geometry of the tissue region, and render the geometrical rendering data to a rendered image using the associated material appearance properties; and a display, configured to present the rendered image.

In some embodiments, the computer circuitry is configured to render the geometrical rendering data using a graphical game engine.

In some embodiments, the interaction data includes sensed positions of the intrabody probe.

In some embodiments, the interaction data includes probe-sensed characteristics of tissue in the vicinity of the probe.

In some embodiments, the interaction data includes treatment status data indicating activation of the intrabody probe to treat tissue.

In some embodiments, the associated material appearance properties are used to simulate interactions of tissue represented by the geometrical rendering data with light.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, some embodiments of the present invention may take the form of a computer program product embodied in one or more computer readable medium(s) having computer readable program code embodied thereon. Implementation of the method and/or system of some embodiments of the invention can involve performing and/or completing selected tasks manually, automatically, or a combination thereof. Moreover, according to actual instrumentation and equipment of some embodiments of the method and/or system of the invention, several selected tasks could be implemented by hardware, by software or by firmware and/or by a combination thereof, e.g., using an operating system.

For example, hardware for performing selected tasks according to some embodiments of the invention could be implemented as a chip or a circuit. As software, selected tasks according to some embodiments of the invention could be implemented as a plurality of software instructions being executed by a computer using any suitable operating system. In an exemplary embodiment of the invention, one or more tasks according to some exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

Any combination of one or more computer readable medium(s) may be utilized for some embodiments of the invention. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium and/or data used thereby may be transmitted using any appropriate medium, including but not limited to wireless, wireline, optical fiber cable, RF, etc., or any suitable combination of the foregoing.

Computer program code for carrying out operations for some embodiments of the present invention may be written in any combination of one or more programming languages, including an object oriented programming language such as Java, Smalltalk, C++ or the like and conventional procedural programming languages, such as the "C" programming language or similar programming languages.

The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Some embodiments of the present invention may be described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example, and for purposes of illustrative discussion of embodiments of the invention. In this regard, the description taken with the drawings makes apparent to those skilled in the art how embodiments of the invention may be practiced.

In the drawings:

FIG. 1A is a schematic flowchart illustrating the iterative rendering and presentation of a simulated tissue having a material appearance dynamically linked to interactions of the tissue with a catheter probe, according to some embodiments of the present disclosure;

FIG. 1B is a schematic flowchart illustrating the iterative rendering and presentation of a simulated tissue having a material appearance dynamically changing over time as a result of prior interaction of the tissue with a catheter probe, according to some embodiments of the present disclosure;

FIG. 1C is a schematic flowchart illustrating the iterative rendering and presentation of a region of tissue undergoing ablation, according to some embodiments of the present disclosure;

FIG. 3 represents a display of a user interface comprising three simultaneously presented visually rendered views, showing a tissue region interacting with a catheter probe, according to some embodiments of the present disclosure;

FIGS. 4A-4C each schematically represent three different views of a tissue region undergoing a sequence of stages of a lesioning procedure, according to some embodiments of the present disclosure;

FIGS. 7A-7C schematically represent dynamically deformable display of the balloon of a balloon-equipped catheter probe in contact with tissue region according to some embodiments of the present disclosure;

FIGS. 8A-8B schematically represent the display of laser light used for ablation of a tissue region, according to some embodiments of the present disclosure;

FIGS. 9A-9B schematically represent dynamically deformable display of a flexible electrode rod of a catheter probe as it interacts with a tissue region, according to some embodiments of the present disclosure;

DESCRIPTION OF SPECIFIC EMBODIMENTS OF THE INVENTION

The present invention, in some embodiments thereof, relates to the field of medical procedures using intrabody probes navigable within intrabody spaces, and more particularly, to presentation of procedure data dynamically acquired during the course of a catheter procedure.

Overview

An aspect of some embodiments of the current invention relates to the motion frame-rate, real-time display of a changing material appearance of simulated tissue, wherein the changes to the material appearance are based on ongoing measurements of interactions between a catheter probe and the actual tissue being simulated.

In some embodiments, a software environment specialized for interactive visual simulations (scene simulations)—for example a 3-D graphical game engine such as the Unreal® or Unity® graphical game engines—is used as a basis for implementing a simulation of a scene comprising the tissue. For rendering to a visual presentation by the game engine's graphics rendering pipeline, material appearances of tissue (that is, the rendered appearance of a tissue simulated as a virtual material) are optionally controlled by one or more material appearance properties (preferably a plurality of such properties), which describe how simulated materials (e.g., simulated materials simulating tissue) interact with simulated optical laws and lighting conditions to generate images for display. It should be understood that one or more capabilities used by some embodiments of the present invention and described as implemented by a game engine are optionally provided by alternative implementations not packaged in a game engine distribution, including: use of customized software, firmware and/or hardware; and/or use of separately distributed software libraries. The term "game engine" as used herein should be understood to encompass computer-implemented collections of such typical game engine capabilities as may be used by some embodiments of the present invention (examples of which are described herein), whether or not they have been packaged into a game engine distribution.

As used herein, the term "rendering" refers to the process of generating an image from a 2-D or 3-D model or models by means of one or more computer programs. The model may contain object parameter definitions and/or data structures; for example, geometry, viewpoint, texture, lighting, and/or shading information as a description of the virtual model. The data contained in the model may be passed to a rendering program to be processed and output to a digital image or raster graphics image file. The processing comprises one or more processing stages referred to collectively as a "pipeline", and carried out by the software and hardware of a rendering device. In some embodiments, the rendering device includes one or more of a general purpose CPU and graphics hardware specialized for use within a rendering pipeline.

Figure 10:
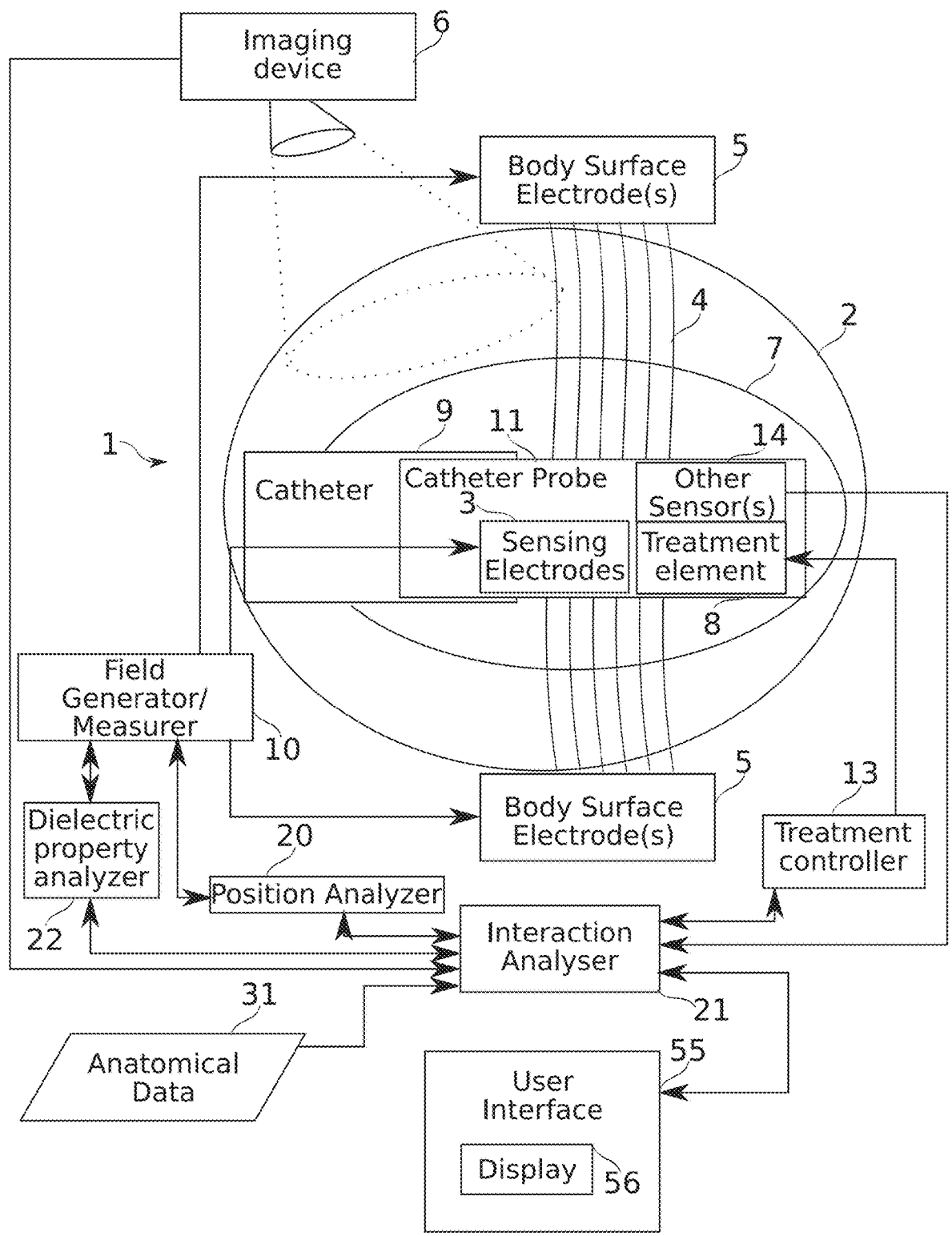
FIG. 10 is a schematic representation of a system configured for display of interactions between a catheter probe and a body tissue region, and/or their effects, according to some embodiments of the present disclosure.
Figure 11:
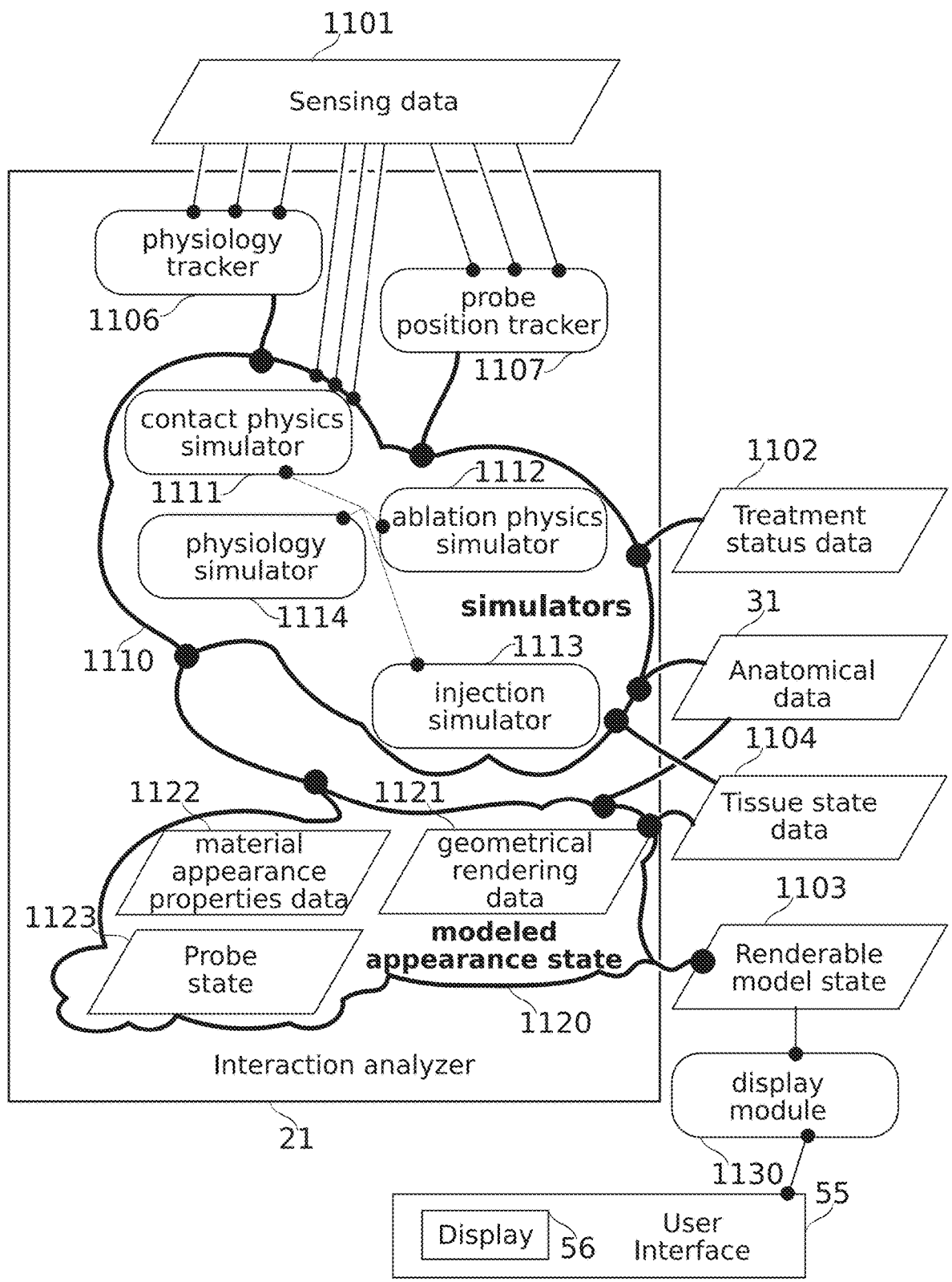
FIG. 11 schematically represents software components and data structures comprised in and/or used by an interaction analyzer of a system, according to some embodiments of the present disclosure.

In some embodiments, updating of the material appearance properties (e.g., to simulate tissue conditions such as edematous or fibrotic) during a catheter procedure is at least partially based on data inputs from one or more data sources supplying data during the procedure (for example, sources of probe-tissue interaction data such as sensing data and/or treatment status data described in relation to FIGS. 10 and 11). Graphical game engines typically receive inputs from game input devices such as pointer devices, keyboards, game controllers, body motion sensors, and the like. In some embodiments of the present invention, inputs optionally are from one or more additional or alternative inputs related to the performance of a catheter procedure—for example, position data indicating catheter probe position (which may be based on measurement data obtained using the probe itself, e.g., measurement of impedances within crossing electrical fields acting to establish a navigational frame of reference), data tracking the intrabody use of catheter probes (particularly but not exclusively use to deliver treatment; e.g. by delivering treatment energies), and/or measurement data other than position data, for example measurement data obtained from an intrabody probe characterizing tissue and/or contact with tissue. Herein a catheter probe is used as an example of an intrabody probe, but it should be understood that another intrabody probe is optionally used in some embodiments; e.g., a capsule probe.

In typical applications of game engines, the simulated world (also referred to herein as a scene) maintained by a game engine do not directly correspond to any simultaneous objective-world state. However, an object of some embodiments of the current invention is to simulate the reality of a clinical situation sufficiently to allow substantially seamless interaction with that reality via a presentation of the scene simulation. In some embodiments, this comprises maintaining (while also presenting) a simulated scene having a useful level of correlation with the changing reality of the actual tissue environment (as reflected in data available to characterize it).

Optionally, usefulness derives from the presentation of the simulated tissue features of the scene informing a catheter operator about the changing state of the tissue environment to allow deciding on actions to be taken. Potentially, the useful level of correlation with the changing reality of the actual tissue environment allows an operator to realize the state of the tissue or a change in that state, optionally without adding to the scene annotations indicative of such state or state change. Optionally, usefulness derives from the presented scene simulation providing sufficient fidelity of representation, so that actions the operator takes based on the presented scene simulation produce effects as intended in the corresponding real-world environment. Optionally, the useful level of correlation with the changing reality of the actual tissue environment is a level of correlation sufficient to allow the operator to perform actions within the real-world environment based on the presented scene simulation. The presented scene simulation may include effects simulating results of the actions taken by the operator. There is also a potential advantage for diagnosis, and optionally planning of treatment in response to the diagnosis, in the transformation of sensed data which is not inherently visual in nature (such as data gathered by an intrabody probe as it maps and/or characterizes tissue) into a visible tissue state, which may assist a physician in integrating data into an overall understanding of the clinical situation.

In some embodiments of the invention, a display of a user interface is updated at motion frame rate with rendered images of a simulation scene simulating an intrabody probe (for example, a probe at the end of a catheter) and its tissue environment. The updating optionally indicates changes to an actual intrabody probe and tissue environment which occur as an operator manipulates the actual intrabody probe (wherein the updating is based, e.g., on position data describing the position of the intrabody probe), and/or operates the intrabody probe for treatment and/or diagnostic measurement of the actual tissue environment (wherein the updating is based, e.g., on operational data describing operation of the intrabody probe to treat tissue and/or measure properties of the tissue). In some embodiments, changes are shown in the rendered images as if occurring within the actual material of the tissue environment.

For example, immediate and/or developing effects of ablation are shown by simulating appearance and/or geometrical changes in ablated tissue (in contrast, for example, to marks, icons, and/or symbols indicating ablation events). In some embodiments, tissue is deflected and/or an intrabody probe shape is deformed in rendered images of a simulation scene based on interaction data indicating contacts. These and other simulation scene changes (for example, other simulation scene changes as described herein) potentially provide an operator with a sense of presence in the actual tissue region accessed by an intrabody probe, and/or intuitive indications of changing status during a procedure underway.

In some embodiments, a smoothly updating, naturalistic scene appearance is achieved even when available inputs indicating changes to the simulation scene are incomplete, slowly updating, irregular, and/or lagging (for example, as described in relation to FIG. 1B). Herein, "naturalistic" scene appearance means that the displayed scene gives an operator the impression of substantial materials (i.e., volume-occupying, as opposed to merely shell defining surfaces) and/or reactive materials existing in a fluidly navigable environment. The reactions of the materials in turn become a significant part of the information which an operator relies on to act within the actual environment that the scene simulates. A material moreover may be simulated as occupying volume per se (for example, as a wall having thickness), rather than merely as a boundary extending in space (for example, as a structure defining a surface, but having no well-defined thickness).

Optionally, appearances of scene objects are moreover "realistic" in some aspects, for example, tissues are provided with material appearances that mimic their appearance in life. However, non-realistic material appearances and even objects are optionally or additionally provided to a naturalistic scene. For example, rendering of blood is optionally suppressed so that visualization is possible. Optionally, one or more normally invisible tissue properties such as temperature are encoded by visual conventions appearing as, for example in the case of temperature: ice, flame, smoke, and/or steam. In some embodiments, guiding marks related to planning and/or procedure progress are optionally provided as part of the naturalistic scene's rendering to images.

In some embodiments of the invention, the correlation between scene simulation and reality is maintained at least in part by treating limited inputs as describing events which (in the real world) entail certain predictable consequences. In the simulated scene, the input optionally acts as a trigger for software routines that simulate those consequences. For example, immediate effects on tissue from energy delivery by a lesioning probe are optionally simulated based on a model of energy dispersion in the tissue (e.g., thermal modeling), and knowing a few parameters about how the energy was delivered (e.g., how long, with what energy, where, and/or with what efficacy). Longer-term effects are optionally simulated by a physiological simulation; for example, a physiological simulation that converts estimated lesion damage into parameters for a script describing the gradual onset of tissue edema.

In some embodiments, moreover, partial and/or occasionally available inputs optionally guide the updating of the simulated scene. In particular but not only, the inputs guide the updating of the material appearance of simulated tissue in the scene. For example, sensing of tissue state directly by the probe (additionally or optionally by a device providing another sensing modality, such as ECG, monitoring of patient hydration, or an intermittently acquired image) is optionally used to update the state of the simulated scene (optionally including updating of one or more of the objects which the simulated scene comprises).

In some embodiments, sensed data is used to update the state of the probe itself, for example, to show the position of the probe, to control the parameters of a simulated viewpoint defined by a position of the probe, and/or to allow a visually simulated probe to change shape (e.g., deform in shape) in response to tissue contacts similarly to the actual probe it mimics; e.g., even if lacking image data that directly show the shape change. The shape may be adjusted based, for example, on a mechanical model of the actual probe and/or a catheter or other device that carries the probe (e.g., a mechanical model which models the flexibility and geometry of the actual probe and/or associated carrying device). For example, some probes such as lasso electrode probes comprise a flexible portion that can be bent in response to the forces of touching contact. In another example, an otherwise stiff probe may be carried on a flexible member such as a catheter used to manipulate it. In some embodiments, sensed input data indicates forces applied to the actual probe, and the simulated probe is modified in response to the indicated forces according to the parameters of the mechanical model. The modification may also take into account other data, for example, a position of the probe itself, geometry of the chamber in which the probe is positioned, and/or a position of an aperture via which a probe is passed into a heart chamber or other body lumen. Potentially, the modeling allows a changing simulated probe shape to indicate changes to the actual intrabody probe in use, without requiring direct measurement of the actual intrabody probe's shape (e.g., by imaging).

A general potential benefit of naturalistic presentation of a scene comprising simulated tissue is to reduce cognitive load on a catheter operator and/or team of operators working with an intra-body catheter. Such procedures typically have multiple interacting factors and requirements affecting procedure outcome that have to be tracked simultaneously and/or with little time for reflection.

Examples of these factors and requirements in a standard operating environment optionally include any one or more of the following:

Positions of one or more probes are selected and verified with respect to a procedure plan.
Results of procedure actions are verified.
If planned actions and actual procedure actions begin to diverge, adjustments may be made on the fly.
Similarly, actual procedure results may not match planned results.
Some parts of the procedure optionally rely on discovering tissue states and locations, for example, based on sensing from the catheter probe.
Such discovery steps are preferably performed quickly and without undue repetition of catheter motions.
Particularly after plan and procedure diverge, relative timing of past procedure steps can be critical for deciding what current and/or following steps are optimal. For example, edema that gradually develops following lesioning (as in certain ablation procedures) can interfere with further lesioning, potentially leading to a need to adjust parameters and/or positions away from those first planned if there is a delay or error in an earlier phase of the procedure.

Similarly, the interpretation of sensing data is optionally dependent on the timing and/or results of previous actions. For example, a detected current impulse block in heart tissue may be correlated with the recent history of lesioning in an area to determine if the impulse block is more likely to be permanent (e.g., pre-existing, or in a well-lesioned area) or temporary (e.g., in a region where inactivation, for example, due to use of a device for administering an ablation modality, is potentially reversible).

In some embodiments of the current invention, immediate visual presentation of material appearance helps to control the complexity these factors can create. Potentially, a naturalistic display of information is more immediately understood by the clinical personnel, and/or intuitively draws attention to clinically relevant state updates. For example, instead of the operator team having to consider and/or calculate whether a previously lesioned tissue region was lesioned long enough ago to have converted to edematous tissue, in some embodiments, the edema is directly displayed by an adjustment to the geometrical appearance of the tissue (for example, by distending the edematous tissue's geometrical appearance to assume a relatively swollen shape). Where a continuous lesion is planned, likely gaps in lesion extent can be directly seen in their overall context in the scene simulation, helping to guide the decision as to whether and/or how the procedure should be adapted to compensate.

A naturalistic presentation of catheter procedure information also contrasts, for example, with the presentation of this information using graphs and/or symbols. Familiarization with more abstract symbols, measures and graphs potentially requires prolonged training. An extra level of symbolic abstraction also potentially slows recognition by the physician of important changes in the state of the catheter interface or the tissue.

An aspect of some embodiments of the current invention relates to the motion frame-rate, real-time display of a changing geometry of simulated tissue, wherein the changes to the material appearance are based on ongoing measurements of interactions between a catheter probe and the actual tissue being simulated.

Among the services provided by some prominent graphical game engines are motion physics simulators (e.g., for modeling collisions, accelerations, elastic deformations, object destruction, and the like). In some embodiments, one or more of these motion physics simulators is used to increase the naturalistic impression of a scene. Additionally or alternatively, geometrical deformations (e.g., of geometrical rendering data, and/or of an appearance thereof rendered to an image; these are described, for example, in relation to FIG. 1A) are used to indicate aspects of a procedure where a probe contacts tissue. As for the case of material appearances, the geometrical deformations may be, but are not necessarily realistic. Degree of tissue compression, for example, is optionally used as a visual proxy for probe-tissue contact force, whether or not the real tissue is indeed compressed. In some embodiments of the invention, geometrical deformation of the simulated scene is directly based on deformation measurements, for example, ultrasound images of septal wall deflection during transseptal puncture are optionally converted into movements in three dimensions of a simulated septal wall's deflection. In some embodiments of the invention, motion due to normal heart pulsations is indicated in the scene simulation by pulses with corresponding timing; this potentially helps an operator understand the difference between a probe in intermittent wall contact and continuous wall contact. Optionally, however, the amplitude of the simulated pulses is reduced from the real state, to stabilize the visual environment an operator uses for navigation.

Before explaining at least one embodiment of the invention in detail, it is to be understood that the invention is not necessarily limited in its application to the details of construction and the arrangement of the components and/or methods set forth in the following description and/or illustrated in the drawings. The invention is capable of other embodiments or of being practiced or carried out in various ways.

Methods and Systems for Visual Modeling of Probe-Tissue Interactions and their Effects Reference is now made to FIG. 1A, which is a schematic flowchart illustrating the rendering and presentation of an image of a simulated tissue having a material appearance dynamically linked to interactions of the tissue with a catheter probe 11 (FIG. 10), according to some embodiments of the present disclosure. While descriptions herein are provided with respect to the use of one probe, it should be understood that interactions of a plurality of probes with tissue are optionally tracked simultaneously and linked to effects on the simulated tissue and/or other scene elements. Further reference is now made to FIG. 10, which is a schematic representation of a system 1 configured for presentation at a user interface 55 (for example, using display 56) of interactions between a catheter probe 11 and a body tissue region 7, and/or effects of these interactions, according to some embodiments of the present disclosure. Reference is also made to FIG. 11, which schematically represents software components and data structures of an interaction analyzer 21 (FIG. 10) of system 1, according to some embodiments of the present to disclosure.

Receipt of Interaction Data

The flowchart of FIG. 1A begins; and at block 110, in some embodiments, an interaction analyzer 21 (of system 1, FIG. 10) receives interaction data acquired from a device (such as a sensing electrode 3 or another probe sensor 14) providing a sensing modality of system 1, and/or operation data of a device (such as a treatment element 8, optionally under the control of a treatment controller 13) providing a treatment modality of system 1. In some embodiments, system 1 is configured for presentation of interactions between a catheter probe 11 and a body tissue region 7, and/or results of such interactions.

The interaction data, in some embodiments, comprise data indicating and/or numerically describing characteristics of interactions between probe 11 and tissue region 7. The interaction data may include, for example, positions of the probe and/or of contacts between the probe and the tissue region, contact characteristics characterizing a contact between the probe and the tissue region, measurements taken by the probe (for example, measurements of tissue state, such as physiological state and/or dielectric properties), and/or actions of the probe (e.g., operations comprising delivery of treatment). Optionally, interaction data comprise imaging data obtained during probe-tissue interactions. System 1 of FIG. 10 indicates examples of sources of interaction data (imaging device 6, sensing electrodes 3, and other sensors 14) which are optionally provided in some embodiments of the present disclosure. Interaction data is optionally received in raw form, or in any suitable stage of intermediate processing to indicate a parameter and/or status of more direct applicability.

With respect to FIG. 10, details for certain types of interaction data available in some embodiments of the invention (e.g., one type, all types, or any other combination of types) are now described for: position data, imaging data, dielectric tissue property sensing, general sensing (for example, of temperature and/or contact force), and treatment interactions.

Position Data:

In some embodiments (optionally), position data is sensed by use of an electromagnetic field navigation subsystem, comprising body surface electrodes 5, field generator/measurer 10, position analyzer 20, and sensing electrodes 3 (for example, sensing electrodes 3 located on catheter probe 11). Here, and elsewhere in this description, position data are data indicating a position of an intrabody probe, and/or position(s) and/or shapes of tissue in the vicinity of the probe. The electromagnetic field navigation subsystem operates by inducing at least one time-varying electromagnetic (EM) field 4 (for example, three crossing EM fields, each of a different frequency) across a region of body 2 including a body tissue region 7 which is targeted to be navigated by catheter 9 and catheter probe 11. Typically, the time varying EM field is induced with a total inter-electrode voltage of one volt or less, at a frequency of between about 10 kHz and about 1 MHz. Voltages sensed at different positions by sensing electrodes 3 are characteristic of corresponding intrabody positions, allowing conversion by position analyzer 20, for example of voltage measurements to position information (for example, after exploration of an intrabody region 7 using the probe 11, and/or initially based on EM fields simulated with respect to a particular configuration of electrodes and anatomical data 31). In some embodiments of the invention, position sensing at least partially comprises sensing of the relative position of a catheter probe 11 and a surface of tissue region 7; for example, by sensing of the dielectric environment of a sensing electrode 3 of catheter probe 11. Optionally, position data indicating a position of an intrabody probe are obtained by another method, for example, magnetic sensing, imaging, and/or ultrasound.

Imaging Data:

In some embodiments, there is provided an imaging device 6, that is, a device configured to collect data by sensing of radiant sound or electromagnetic energy to produce an image that comprises imaging data. Imaging device 6 is distinguished from other sensor(s) 14 by being located outside the region being imaged. Examples of imaging device 6 may include, for example, an ultrasound device and/or a fluoroscopy device. Imaging device 6 is configured to monitor body tissue region 7 during use of the catheter probe, providing imaging data as an output. Characteristics which may be monitored by means of the image data output of imaging device 6 optionally comprise additional or alternative position data for the probe and/or of tissue in the vicinity of the probe, for example, tissue affected by operation of the probe. Tissue characteristics suitable for imaging (for example, uptake of tracing agents and/or contrast with tissue of other types) may also be monitored. In some embodiments, the imaging device is in continuous, real-time (e.g., 5, 10, 15, 20, 30, 60 or more images per second) use during at least some phase of a procedure. Optionally, system 1 continuously processes changes in images produced by imaging device 6 for immediate display (within a few milliseconds, for example, within 250 milliseconds) at user interface 55.

Additionally or alternatively, in some embodiments, imaging device 6 operates less frequently (for example, once every minute to every five minutes, or at another interval). Infrequently updating imaging devices 6 are optionally used for providing periodic "key frames" used to synchronize and/or verify display of simulated states of tissue region 7 and/or catheter 9. Optionally, imaging information provides indirect information about elements in the scene simulation—for example, displacement of an organ boundary imaged with relatively high contrast optionally provides information about the displacement of a less clearly visualized organ in communication with the organ boundary. Also for example, data imaged in a tissue cross-section optionally provides information which can be extrapolated to regions outside of the cross-section.

Dielectric Tissue Property Sensing:

In some embodiments, dielectric property measurements (e.g., measurements of impedance under time-varying electrical fields) providing indications of tissue state, and/or of tissue-probe contacts, are made by dielectric property analyzer 22. The measurements, in some embodiments, use sensing electrodes 3 (or a subset thereof) to sense electrical fields generated in conjunction with field generator/measurer 10, and optionally body surface electrodes 5. In some embodiments, dielectric property sensing is used to distinguish, for example: the state of tissue as healthy, fibrotic, edematous, charred or charring, and/or electrophysiologically active (or capable of being so, e.g., retaining cellular integrity after attempted ablation). In some embodiments, dielectric property sensing identifies and/or verifies tissue type(s) in a sensed region. Dielectric property sensing for such properties is described, for example, in International Patent Application Nos. PCT/IB2016/052690 and PCT/IB2016/052686, the contents of which are incorporated by reference herein in their entirety.

General Sensing:

In some embodiments, other sensed data (sensed by optional other sensor(s) 14 on catheter probe 11) is used as interaction data. For example, a force sensor may provide information on contact between a catheter probe 11 and its environment. The information may include indication that the contact has happened, and optionally with what degree of force. Additionally or alternatively, contact quality and/or contact force information is provided from sensing electrodes 3, based on impedance measurements and/or sensing of dielectric properties. For example, where a surface of tissue region 7 and an electrode 3 of a catheter probe 11 are in contact, dielectric sensing optionally is used to provide an indication of contact quality (optionally as related to a corresponding contact force), for example as described in International Patent Application No. PCT/IB2016/052686, the contents of which are included by reference herein in their entirety. Contact quality may include dielectric and/or impedance sensing of the tissue environment of one or more electrodes, based on which force, pressure, area, and/or angle of contact between electrodes and the tissue environment is inferred, relatively and/or absolutely.

In some embodiments, other sensor(s) 14 comprise a temperature sensor, flow sensor, and/or another sensor configured to provide information about the environment of the catheter probe 11.

Treatment Interactions:

In some embodiments, a treatment element 8 is provided on catheter probe 11. The interaction data (for example, treatment status data 1102 of FIG. 11) optionally comprises information about the operation of the treatment element and/or components controlling its effect (for example, power levels, activation events, timing settings, and/or substance amounts administered).

Treatment element 8 is optionally a probe for ablation treatment by administration of an ablation modality to form a lesion; for example, using one or more of the following ablation modalities: radio frequency ablation, cryoablation, microwave ablation, laser ablation, irreversible electroporation, substance injection ablation, and/or high-intensity focused ultrasound ablation. In some embodiments, treatment element 8 is also used as a sensing electrode 3 (for example, in RF ablation, a treatment delivery electrode may also be used to sense the effect of local dielectric properties on measured electrical field impedance). Optionally, treatment element 8 is operated in conjunction with a treatment controller 13, configured to provide treatment element 8 with functions such as power, control (e.g., of signal frequency, phase, and/or timing), and/or monitoring. In some embodiments, the treatment element 8 is configured to deliver a treatment other than ablation (for example, temporary activation or inactivation of tissue activity) using heat, cold, electrical current, sound radiation and/or light radiation. Optionally, treatment element 8 comprises an injection apparatus, used to inject a treatment substance, and/or a substance used in diagnosis such an imaging tracer. In some embodiments, the injected substance comprises ethyl alcohol, Botox, living cells, and/or growth factor. Optionally, the injected substance comprises a radiolabeled substance, an immunosubstance, and/or a radiopaque trace substance. Optionally, treatment element 8 comprises a tool for manipulating tissue (e.g., grasping, holding, sampling, cutting, attaching, and/or suturing). Data indicating operations of treatment element 8 (and/or the rest of a device providing a treatment modality, for example, including a treatment controller 13) are optionally available within system 1, and in particular available to modules of interaction analyzer 21, as treatment status data 1102 (FIG. 11). It should be understood that treatment status data 1102 are not limited strictly to data about operations targeted to disease treatments as such, but optionally also include administration of substances and/or energy affecting a tissue region for a diagnostic purpose.

Interaction data relating to the interactions of a treatment element 8 with a target tissue region 7 include, for example, duration of operation, time of operation, power and/or frequencies of energy delivered, nature and/or concentration of substances delivered, and/or quantities of substances delivered. Optionally, operational settings are combined with information about the position and/or environment of treatment element 8 in order to derive interaction data. In some embodiments, such combination is performed by one or more of simulators 1110 of FIG. 11.

It should be understood that not every source of interaction data described in relation to FIG. 10 is necessarily implemented in every embodiment of the invention. Preferably, there is provided in embodiments of the invention at least a device providing a position sensing modality (e.g., comprising position analyzer 20), and a device providing a treatment modality which is monitored through treatment status data (e.g., comprising treatment controller 13). In FIG. 11, sensing data 1101 optionally includes data from one or a plurality of sensing devices; for example, sensor electrodes 3, other sensors 14, and/or imaging device 6, described in relation to FIG. 10.

Moreover, it should be understood that computation-performing and/or control operation-performing components indicated, e.g., in FIG. 10, are optionally implemented by any suitable combination of shared and/or dedicated processing units and/or controllers. For example, implementations of treatment controller 13, position analyzer 20, and/or interaction analyzer 21 optionally comprise one shared processing unit, or any other suitable number of shared and/or dedicated processing units.

Optionally, the flowchart continues with block 112. In some embodiments, certain types of interaction data (such as inputs indicating onset of ablation treatment) branch to FIG. 1B (dotted line branch indicates optional branching).

Material Appearance Properties

At block 112 of FIG. 1A, in some embodiments, material appearance properties are optionally assigned (by selection or calculation, for example) to geometrical rendering data, and more particularly to locations within a 3-D data structure of the geometrical rendering data representing geometry of the targeted body tissue region 7. The operations of block 112 are carried out, in some embodiments, by interaction analyzer 21.

Herein, the 3-D data structure to which material appearance properties are assigned is generically referred to as geometrical rendering data 1121. In some embodiments, geometrical rendering data 1121 comprise mesh data; for example as is commonly used in defining structures for computerized visual rendering of 3-D structures. Geometrical rendering data 1121 specify positions (and usually also connections among positions, and/or positions joined by the extent of a common surface and/or material volume), corresponding to positions of surfaces of a target body tissue region to be visually rendered for presentation. Optionally, the geometry of positions interior to the surface is also represented (for example, where presentation includes the use of transparency and/or cross-sectional views). Surfaces represented are optionally external (e.g., organ surfaces; not necessarily surfaces visible externally to the body) and/or internal (e.g., lumenal) surfaces of the target body tissue region. In some embodiments, geometrical rendering data 1121 are derived from anatomical data 31; for example, appropriately segmented 3-D medical image data. In some embodiments, anatomical data 31 include specification of tissue region thicknesses, for example, thicknesses of heart walls. Heart wall thickness is optionally obtained from, for example: atlas information (optionally for a population corresponding to the current patient), modified atlas information (for example, scaled according to anatomical landmark correspondence, heart rate, and/or observations at selected positions), and/or imaging of the patient (for example, one or more of CT, MRI, and/or nuclear imaging techniques).

In some embodiments, the appearance of the raw geometrical rendering data 1121 that is finally presented (for example on display 56) by a user interface 55 is determined in part by the assignment, to positions defined by the geometrical rendering data, of material appearance properties (MAPs). As the term is used herein, MAPs comprise any properties associated to positions (typically positions occupying an extent of a "virtual material", as next described) in a virtual environment for visual rendering according to simulated optical laws, and which affect how a surface and/or its enclosed volume are visualized within a 3-D rendered space. For example, MAPs may define color, texture, transparency, translucency, scattering, reflectance properties, and the like (more specific examples are described hereinbelow). MAPs are usually but not only assigned to surface positions of the geometrical rendering data. MAPs are optionally assigned to volumes defined by surfaces of the geometrical rendering data 1121. MAPs can also be assigned to the virtual environment (e.g., as lighting parameters) in such a way that they affect material appearance.

Creating the visual rendering in some embodiments may include rendering of surfaces and/or volumes comprising "virtual material". A virtual material, in some embodiments, is defined to occupy an extent within a simulated geometrical space (e.g., is defined by geometrical rendering data), and is subject (on its surfaces and/or within its volume) to simulated optical rules approximating processes such as reflection, scattering, transparency, shading, and lighting. Not every optical rule used in visual rendering is a copy of a real-world physical process; the art of computer rendering includes numerous techniques (for achieving both realistic and deliberately unrealistic results) that apply simulated optical rules that have no direct physical equivalent. For example, bump mapping simulates surface height irregularities by manipulation of reflectance. Ambient occlusion is an efficiently calculable lighting effect defined in association with surface maps, wherein light sources are treated as approximations.

Optionally, a MAP is defined other than as a property of a virtual material as such. For example, in some embodiments, certain effects of lighting are implemented using sources which are virtually placed remote from a surface they illuminate (and so, not defined as properties of the surface's virtual material, while still affecting the material appearance).

A virtual material optionally also defines material properties that are not directly "of appearance", for example, density, viscosity, thermal properties, and/or elastic properties. However, insofar as these properties do in turn (in a given embodiment) affect the definition of MAPs (for example, via calculations of one or more simulators 1110), they are optionally treated as parts of material appearance properties data 1122, without actually comprising MAPs in themselves. Additionally or alternatively, non-appearance properties, particularly those that affect how geometry changes for example, deforms, are optionally considered part of the geometrical rendering data 1121. These properties include, for example, thickness, density, velocity, viscosity, and/or elasticity.

Optionally, baseline MAPs data 1122 are initially assigned to surfaces (optionally, volumes) defined by the geometrical rendering data 1121 so that these surfaces resemble, when suitably rendered for visual presentation by user interface 55, simulated versions of the tissue they represent. Optionally, this comprises associating MAPs data which provide a visual texture indicative of the tissue structure of which the body tissue region is comprised. For example, a muscular organ such as the heart is optionally rendered as a mottled reddish-pink, optionally with additional surface properties such as scattering, roughness, specular reflection properties, and/or overall reflectivity defined to give it irregular gloss evocative of a wet surface. Highly vascular structures such as liver and kidney tissue are optionally represented with a more uniform and ruddier hue. Fibrotic tissue is optionally, for example: duller, greyer, lighter, and/or dryer in appearance; may be thinner (e.g., giving an appearance of being relative recessed from surrounding tissue) and optionally is textured with surface irregularities indicative of scarring.

Optionally, baseline MAPs data takes into account tissue state data 1104 which characterizes tissue beyond its geometrical shape. In some embodiments, for example, 3-D nuclear imaging data is optionally used to distinguish between healthy and scarred cardiac muscle tissue, and the respective cardiac muscle tissues are associated with tissue state data indicative of their state being "healthy" or "scarred". Scarred tissue is optionally distinguished in presentation by differences in one or more virtual optical properties from healthy tissue (e.g., rougher, duller, and/or grayer in appearance).

In some embodiments of the invention, MAPs are defined and/or modified from baseline based on changes in tissue, wherein the changes are calculated from interaction data. Optionally, the change in MAP definition imitates appearance changes which the interaction data suggest are occurring in the actual tissue. In some embodiments, these effects relate to blood or scattering properties: for example, ablation effects which tend to block or interrupt blood flow optionally are modeled by the selection of lighter, grayer, and/or yellower MAPs; while effects leading to increased blood flow (for example, inflammation) are optionally modeled by selection of MAPs which imitate more closely the appearance of blood (e.g., spectral characteristics of hemoglobin). In another example, interaction data indicating tissue coagulation or other structural disordering (lesioning) leading to increased frequency non-specific optical scattering are optionally translated into MAPs which are whiter and/or grayer. Additionally or alternatively, other visual texture characteristics are adjusted; for example, alterations to MAPs governing visual roughness and/or specular reflection are made (e.g., ablated tissue becomes "dull" and/or edematous tissue becomes "smooth"). In some embodiments, newly assigned MAPs simply replace older MAPs. In some embodiments, newly assigned MAPs overlay and/or are composited with older MAPs. For example: existing MAPs are modified by a change in one or more parameters (e.g. MAPs affecting color), while other parameters (e.g., MAPs affecting texture) remain fixed; new MAPs are composited with existing MAPs by use of partial transparency; and/or new MAPs are composited with existing MAPs by interpolation of parameter values between them.

In some embodiments of the invention, a change in MAP definition is made when new information enhances previously available data relating to how tissue appears and/or is structured. For example, in some embodiments, measurements made using dielectric mapping allow distinguishing partially fibrotic heart tissue regions from both completely healthy, and completely fibrotic regions. The inventors have found that impedance measurements assessing tissue state, for example as described in International Patent Application No. PCT/IB2016/052690, can in some cases detect fibrotic "striping", wherein bands of fibrotic tissue are intercalated with active muscle tissue. The striping may be detected due to differences in dielectric properties between the two tissues, and/or due to corrugation (periodic differences in tissue height) causing changes in a quality of probe-tissue contact. Optionally, striping of fibrotic regions is represented in the MAP definition by a suitable corresponding visual indication, such as alternating bands of healthy-colored and fibrotic-colored (e.g., more reddish and more greyish, respectively) tissue.

Optionally, for example as new mapping data becomes available, fibrotic striping is shown in the rendered image using fine-scale assignment of MAPS which alternately indicate fibrotic and healthy tissue—and directly, according to whether or not the particular region of tissue shown is measured to be fibrotic or healthy. For example, to fibrotic tissue is optionally assigned MAPS having one or more of the visual characteristics (texture and/or color, for example) of a lesion, while intercalated health tissue is assigned health muscle-appearance MAPs. Optionally, an appearance of relatively raised and recessed stripes is defined by the MAPs, and/or assigned to the geometrical rendering data (indicating, for example, relative atrophy in fibrotic tissue regions).

In some embodiments, fibrotic striping is identified as existing generally within a dielectrically mapped region of tissue, without necessarily identifying precise locations of each stripe. Optionally, MAPS are defined for a region which provide it with a fibroticly striped texture (e.g., corrugated and/or with periodic color differences) and the MAPS assigned to indicate the overall status of the region as partially fibrotic, without special care taken to display exact positioning of the intercalated fibrotic/healthy segments of the tissue.

MAP changes in response to interaction data are not necessarily limited to approximations of actual tissue appearance (appearance "as it would really be" ignoring the presence of blood, other organs, restricted lighting, and the like). For example, changes in MAP from baseline are optionally exaggerated for clarity. Changes in MAP from baseline are optionally chosen to reflect conventions or expectations of how an interaction affects tissue. For example, even if an already well-perfused tissue does not actually become "redder" when inflamed, it is still an option, in some embodiments, to apply MAP reddening over an existing texture comprising, e.g., color shift, brightening, and/or increase in saturation to indicate an inflamed state. Similarly, heating and cooling are optionally indicated by assigning "redder" or "bluer" MAPs; adding an icy gloss to cooled-off tissue; adding smoke, glow, and/or flame to heated tissue; etc. Any of these MAPs changes are optionally implemented by compositing the change-indicating MAPs with existing MAPs of the tissue, for example, MAPs that indicate tissue structure. In another example, the surface of a region injected with a substance such as Botox® (Allergan, Inc., Irvine Calif.) is optionally represented as having MAPs which give it a "smoother" appearance (e.g., bump map texturing is suppressed), whether or not smoothness relates to a realistic appearance change.

In a further example, representation of tissue which interaction data suggests is undergoing some relevant change is optionally changed to have MAPs conveying coruscating (for example), or another non-physiological, yet suggestive, appearance. In some embodiments, MAPs are defined using light source positioning, for example, to selectively illuminate (e.g., by imitation in the scene simulation of a laser or flashlight light beam) a tissue region.

In another example, a non-opaque medium (for example a medium occupying the virtual space of a lumen through which a catheter 9 is navigated) is assigned values for properties such as scattering, transparency, and/or absorption which are not fully transparent. For example, regions where actual positions and/or tissue properties are uncertain are optionally shrouded behind a semitransparent volume rendering as fog, smoke, haze, modified color, or another effect of a semitransparent medium. As for the examples of lighting, this optionally comprises a MAP having an underlying definition in data and/or software which is positioned outside the virtual material of a surface whose display appearance is affected.

In another example that illustrates a difference between use of symbols (e.g., as a part of an image overlay superimposed on a rendered image) and renderings within a simulated visual environment: tissue targeted for a treatment procedure such as ablation is optionally rendered with MAPs defining a pattern (e.g., a circle) indicating that it is a target. The change in MAPs definition is distinguished from a simple overlay, in that it retains the reactiveness of a material surface to its virtual environment (e.g., the material's appearance changes in response to a change in simulated lighting, shading, and/or view angle).

Examples of MAPs are also described in relation to other figures herein, for example, FIGS. 2A-2E, 3, 4A-4C, 6A-6C, and 8A-8B.

Assignment of MAPs to Geometrical Rendering Data

In some embodiments of the invention, material appearance properties are assigned based on the output of one or more simulators 1110 (FIG. 11).

In some embodiments, sensing data 1101 and/or treatment status data 1102 (i.e., data describing the operation of device for administering a treatment modality) are used directly or indirectly as input to one or more simulators 1110 (e.g., simulators 1111, 1112, 1113, and/or 1114) that make adjustments to a modeled appearance state 1120 of the tissue based on inputs received, and one or more simulated aspects of tissue physiology, geometry, and/or mechanics. The modeled appearance state 1120 includes the geometrical to rendering data 1121 and material appearance properties data 1122 in a form suitable for being operated on by the simulators 1110; it may also be or comprise a renderable model state 1103 suitable for rendering for presentation, or else be convertible to a renderable model state 1103. In some embodiments, modeled appearance state also includes data indicating the probe state 1123.

Simulators 1110 also optionally receive as starting input anatomical data 31 and/or tissue state data 1104. In addition to adjusting the modeled appearance state 1120, simulators 1110 optionally maintain their own internal or mutually shared state data. Operations of some exemplary simulators 1111, 1112, 1113, and 1114 are described in the context of the examples of FIGS. 2A-2E, 3-4C, and 5A-5B (relating, for example, to RF ablation), FIGS. 5A-5B (relating more particularly to thermal simulation), FIGS. 5C-5D, 7A-7C, and 9A-9B (relating to the simulation of mechanical contact and motion), FIGS. 6A-6B (relating to the simulation of tissue states such as hidrosis and/or edema), FIG. 6C (relating to the simulation of injection treatments), and/or FIGS. 8A-8B (relating to the simulation of laser treatments).

In relation to FIG. 11, different input types providing probe-tissue interaction data as input to simulators 1110 are now described, including direct sensing input, physiologically interpreted sensing input, positionally interpreted sensing input, and treatment status input. In some embodiments, the inputs comprise direct and/or transformed use of one or more of the interaction data types described in relation to block 110.

Direct Sensing Input:

In some embodiments, adjustment of the simulation scene is implemented based directly on sensing data 1101. For example, a temperature reading from a temperature sensor 14 is optionally mapped directly to a color change selected according to the measured temperature.

Physiologically Interpreted Sensing Input:

In some embodiments, the use of sensing data 1101 by a simulator is indirect. For example, the sensing data may be used after being interpreted by one or more physiology trackers 1106. Physiology tracker 1106, in some embodiments, is a module which accepts sensing data 1101 and generates an assessment of current physiological state based on the sensing data 1101. For example, in some embodiments, sensing data 1101 comprises dielectric measurements that physiology tracker 1106 is configured to convert into assessment of tissue state, for example fibrotic, healthy, or edematous; for example as described in International Patent Application No. PCT/IB2016/052690, the contents of which are included by reference herein in their entirety. Optionally or alternatively, electrical activity originating in tissue (e.g., pacing signals) indicates a functional state of the tissue (e.g., general capacity to support electrical propagation, and/or feature of the electrical activity itself such as strength or timing), and is measured and used as sensing input.

The output of the physiology tracker 1106 from one or more of these inputs is optionally in terms of one or more states such as lesion depth, lesion volume, degree of lesion transmurality, characterization of tissue edema, characterization of functional activity and/or inactivation, a classification as to a potential for tissue charring, and/or a classification as to a potential for or occurrence of steam pop. "Steam pop" is a phenomenon occurring during ablation with an audible popping noise and/or spike in impedance, which is apparently due to sudden release of steam after excessive heating, associated with risk of perforation. These outputs are optionally provided to a physiology simulator 1114 and/or an ablation physics simulator 1112, configured to convert such states into MAPs that indicate the state calculated from the measurements. Optionally, the tissue state interpreted from the sensing input also affects mechanical properties assumed, for example, by a contact physics simulator 1111 and/or an injection simulator 1113. It is a potential advantage to implement a physiological tracker 1106 as a distinct module that can be treated as a computational "service" to any appropriate simulator 1110. However, it should be understood that physiological tracker 1106 is optionally implemented as part of one or more simulators 1110 producing changes to a modeled appearance state 1120. In this case, the module configuration is more like that of direct sensing input, with the simulation of appearance integrated with physiological interpretation of the sensing data.

Positionally Interpreted Sensing Input:

In some embodiments, the use of sensing data 1101 by a simulator is indirect. For example, the sensing data may be used after being interpreted by a probe position tracker 1107. Probe position tracker 1107, in some embodiments, is a module that accepts appropriate sensing data 1101 (e.g., electromagnetic field navigation data, acoustic tracking data, and/or imaging data) and converts such measurements to a determination of the position (e.g., location and/or orientation) of a probe such as catheter probe 11, for example as described in International Patent Application No. PCT/IB2016/052687. It optionally comprises position analyzer 20. Optionally, position tracker 1107 implements processing to massage outputs of position analyzer 20 in view of the current state of the simulated scene—for example, to calibrate sensed position data to positions compatible with the scene simulation. Optionally, position tracker 1107 integrates positioning data from a plurality of position inputs.

Optionally, position determination includes determination of tissue contact force and/or quality, using a force sensor on the probe, and/or for example as described in International Patent Application No. PCT/IB2016/052686, the contents of which are included by reference herein in their entirety. Additionally or alternatively, on-line imaging data (e.g., ultrasound and/or angiographic images) are used, intermittently and/or continuously, to determine and/or verify probe position.

Probe position determinations are optionally used as inputs to any of simulators 1110; for example in order to assign particular positions to measurements of other tissue states/properties, and/or to help characterize changes induced by probe interactions with tissue (e.g. re-shaping tissue geometry, and/or effects of treatment procedures). It may be a potential advantage to implement probe position tracker 1107 as a distinct module that can be treated as a computational "service" to any appropriate simulator 1110. However, it should be understood that probe position tracker 1107 is optionally implemented as part of one or more simulators 1110 producing changes to a modeled appearance state 1120 maintained by interaction analyzer 21.

Treatment Status Input:

In some embodiments, simulation is implemented based on treatment status data 1102. Treatment status data 1102 include data indicating the administration of a treatment modality and/or a status of a device for administering the treatment modality—for example, power, control parameters (e.g., of signal frequency, phase, and/or timing), and/or monitoring data. Optionally, treatment status data are applied directly to modeled appearance state 1120; for example, as a mark at each position of treatment. Additionally or alternatively, in some embodiments, at least one aspect of the tissue and/or tissue/probe interaction is physically and/or physiologically simulated in order to produce a new modeled appearance state 1120, based on the treatment status data. For example, in some embodiments, a physiology simulator 1114 receives input indicating that a probe-delivered treatment operation has occurred at some particular position (optionally along with parameters of the treatment operation). Physiology simulator 1114 is optionally configured to model the reaction of tissue to the treatment, instantaneously (for example, due directly to energy delivered by an ablation treatment), and/or over time (for example, as an edematous reaction develops in the minutes following an ablation treatment). In another example, an injection simulator 1113 receives treatment status data indicating that a material injection is occurring. Injection simulator 1113 is optionally configured to model an appropriate reaction of tissue to the injected substance (e.g., ablation and/or inactivation). The reaction is optionally immediate, and/or includes a slow-developing component as the material diffuses from the injection site. Optionally, changes in geometry due to the addition of material volume to the tissue are also modeled.

Presentation of Visual Rendering

At block 114, in some embodiments, a visual rendering of the modeled appearance state 1120 is presented.

In some embodiments of the invention, a modeled appearance state 1120 is converted to a renderable model state 1103 and provided to a display module 1130 that converts (renders) the renderable model state into at least one image comprising a visually rendered representation of the intra-body region 7. Optionally, modeled appearance state 1120 is directly represented as a renderable model state 1103. The at least one image is optionally displayed by user interface 55. Use of a modeled appearance state directly represented as a renderable model state provides a potential advantage for tighter integration of the simulation with a game engine driving its rendering and presentation. The at least one image is displayed by one or more graphical displays of a user interface 55. User interface 55, in some embodiments, comprises one or more displays 56, for example a computer monitor, virtual reality goggles, and/or 2-D or 3-D projection device. Preferably, user interface 55 also comprises one or more user input devices that can be used for tasks such as selecting operating modes, preferences, and/or display views. It is noted that insofar as catheter probe position sensing affects simulation and/or display, catheter probe manipulation also acts as a special form of user input device; but for purposes of the descriptions herein such catheter probe sensing inputs should be considered distinct from inputs provided through user interface 55.

In some embodiments, display module 1130 renders from one, two, three, or more simulated viewpoints simultaneously. In some embodiments, rendering is performed (and images are displayed) at a frame rate sufficient to produce perceived motion (herein, such a frame rate is termed a motion frame rate)—for example, at least 10-15 frames per second; and optionally at least, for example, 15, 20, 30, 50, 60, or 100 frames per second (fps), or another greater or intermediate value. Within this range, lower frame rates (e.g. 10-20 fps) tend to give the appearance of "choppy" motion, with apparent motion growing increasingly fluid with rates up to at least 30-60 fps. More fluid motion is potentially less fatiguing and/or more precise for guiding actions based on events in the simulation scene. Still higher frame rates (above the nominal frequency of visual flicker fusion) add the potential advantage of increasingly convincing presentation of very rapid motion (e.g., reducing visual appearance of discrete-position motion "trails"). Trans-flicker fusion frequency frame rates are optionally preferred for immersive, virtual reality (VR) user interface implementations; higher frame rates potentially help mitigate VR motion sickness.

Updating of the underlying model appearance state 1120 itself is optionally at any suitable rate. For example, the model appearance state 1120 is optionally refreshed, for example, about every minute, ten seconds, three seconds, or second; or at about 2 Hz, 5 Hz, 10 Hz, 15 Hz, 60 Hz, or 100 Hz optionally, receiving new interaction data results in an interrupt event, which triggers updating of model appearance state 1120. Updates to model appearance state 1120 optionally are based on new interaction data, and/or on the development of processes triggered by previous interaction data.

In some embodiments of the invention, display module 1130 includes a computer-implemented software module comprising the rendering pipeline 1230 of a 3-D graphics engine 1200 (software environment) such as is provided with graphical game engines such as the Unreal® or Unity® graphical game engine. Optionally, the conversion of a modeled appearance state 1120 into a renderable model state 1103 comprises the creation and/or instantiation of computer data and/or code structures that are directly used by the rendering pipeline of the 3-D graphics engine 1200.

Optionally, some functions of interaction analyzer 21 (for example, any of simulators 1110) are provided as functions (e.g. classes, hook implementations, etc.) making use of the application programming interface (API) of such a 3-D graphics engine 1200.

At block 116, in some embodiments, flow optionally returns to block 110 to receive more interaction data, or else (if adaptive visual rendering is to be suspended), the flowchart ends.

Use of a Graphical Game Engine in Real-Time Anatomical Presentation

Figure 12:
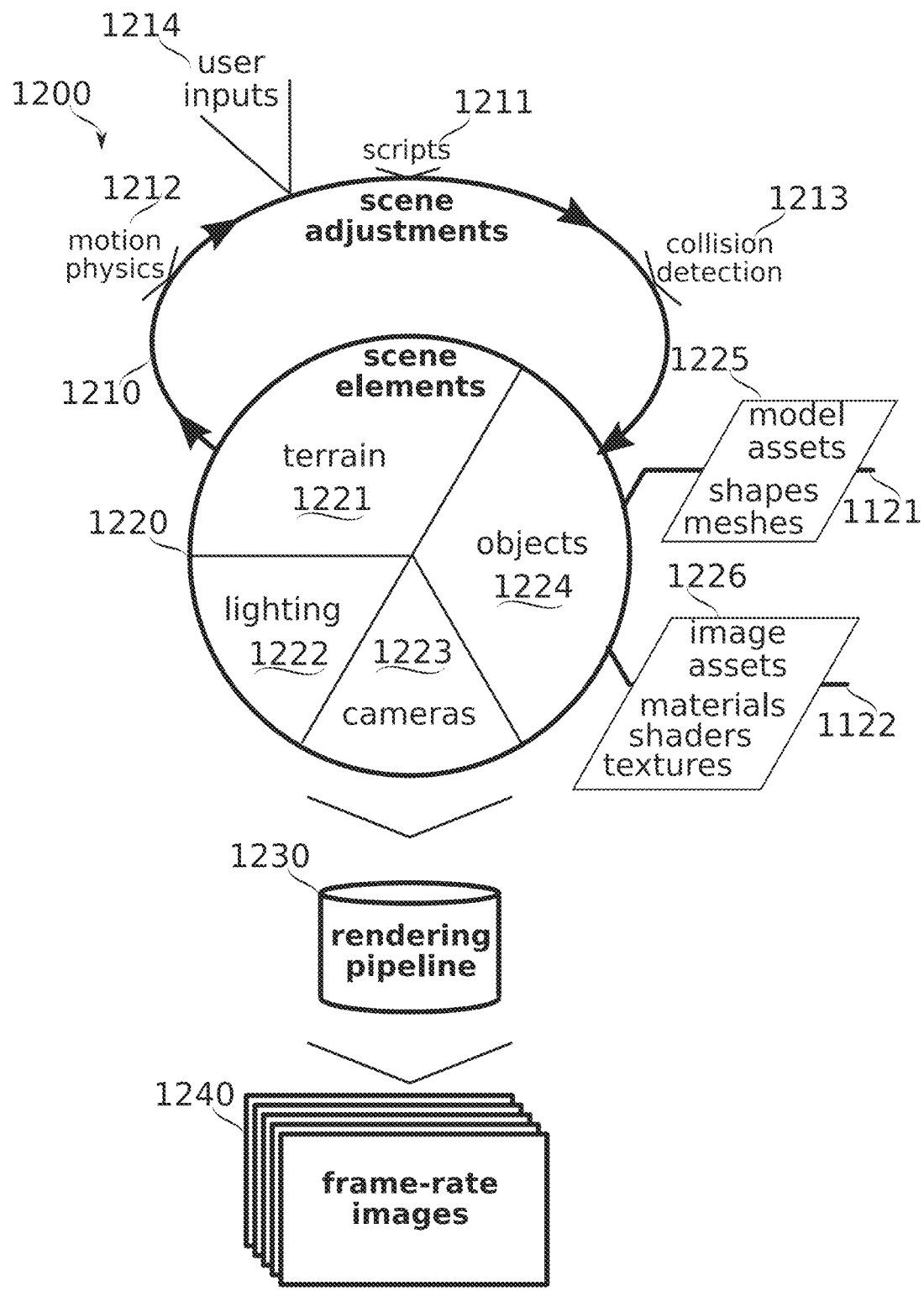
FIG. 12 schematically represents components, inputs, and outputs of a graphical game engine operating to manage and render scene elements to motion frame-rate images, according to some embodiments of the present disclosure.

Reference is now made to FIG. 12, which schematically represents components, inputs, and outputs of a graphical game engine 1200 operating to manage and render scene elements 1220 to motion frame-rate images 1240, according to some embodiments of the present disclosure.

In some embodiments of the invention, a graphical game engine 1200 is used not only to render images (for example as described in relation to block 114 of FIG. 1A), but also to provide more generally the data structure and code framework of the "scene" and how it changes in response to time and input.

In broad outline, a graphical game engine 1200 comprises a collection of computer software components exposing one or more application programming interfaces (APIs) for use in describing, instantiating (initializing and maintaining), continuously updating, rendering, and/or displaying of scene elements 1220. The scene elements 1220 provided for the operations of graphical game engine 1200 optionally include, for example, descriptions of terrain 1221, objects 1224, cameras 1223, and/or lighting elements 1222. In some embodiments of the present disclosure, definitions of scene elements 1220 are derived from geometrical rendering data 1121 and/or MAPs data 1122. Definitions are optionally expressed in terms of geometrical-type scene data 1225 (e.g. model assets, shapes, and/or meshes), and/or appearance-type scene data 1226 (e.g., image assets, materials, shaders, and/or textures). In some embodiments, geometrical rendering data 1121 and MAPs data 1122 are initially produced already in a format that is directly used by graphical game engine 1200.

In some embodiments, scene elements 1220 are provided with simulated dynamic behaviors by an iterated series of calculated scene adjustments 1210. Scene adjustments 1210 are optionally implemented by a variety of software components for e.g., motion physics service 1212, collision detection service 1213, and/or scripts 1211. These are examples; graphical game engines 1200 optionally implement additional services, e.g., "destructibility". Scripts 1211 can be provided to simulate, for example, autonomous behaviors and/or the effects of triggered events. Scripts 1211 are optionally written in a general-purpose computer language taking advantage of APIs of the graphical gaming engine 1200, and/or in a scripting language particular to an environment provided by the core graphical gaming engine 1200. Graphical gaming engines optionally also accept integration with plugin software modules (plugins, not shown) that allow extending the functionality of the core graphical game engine 1200 in any of its functional aspects. For purposes of the descriptions provided herein, plugins that perform functions related to updating the scene state are also encompassed within the term "script" 1211. In some embodiments, all or part of any of simulators 1110 is implemented as a script 1211.

For purposes of descriptions herein, scripts 1211 (optionally including plugins) and scene elements 1220 are considered part of the graphical game engine 1200 as a functional unit. Optionally, for example, where reference is made particularly to the off-the-shelf graphical game engine apart from specialized adaptations for uses described herein, the term "core graphical game engine" is used.

For interactivity, graphical game engines 1200 accept user input 1214 (optionally including, but not limited to, inputs from user interface 55 devices such as mouse, keyboard, touch screen, game controller, and/or hand motion detector; and for some embodiments of the current invention, optionally including data provided as input that indicate probe positions, operation of a device providing a treatment modality, etc.)

A typical graphical game engine may also include a rendering pipeline 1230 that may include one or more stages of 3-D rendering, effects application, and/or post-processing, yielding at least one stream of frame-rate images 1240. In some embodiments, the stages of the rendering pipeline 1230 include modules that implement simulated optical algorithms—not necessarily directly based on real-world physical laws-generally selected to produce a rendered result that visually gives to elements in the rendered scene the appearance of material substances.

Table 1 includes some examples of how graphical game engine features and concepts are optionally used in some embodiments of the current invention.

TABLE 1

Examples of Graphical Engine Feature/Concept Usage

| FEATURE/CONCEPT | EXAMPLES OF USE |
| --- | --- |
| Scene | Overall visually renderable model of environment and objects within it. Optionally equivalent to a renderable model state 1103 and/or a collection of scene elements 1220. |
| Terrain | Optionally used to represent geometry of the anatomical environment; e.g., geometrical rendering data 1121. For example, the heart wall might be implemented as terrain 1221 (alternatively, anatomical features are implemented as objects 1224; e.g., as mesh geometry objects, and/or combinations of primitive objects such as cylinders, boxes, and/or ellipsoids). |
| Objects 1224 | Probe 11 is optionally represented as a "game" object, and may optionally serve as a viewpoint anchor like avatars and/or tools in certain 3-D games. Significant features of the anatomical environment such as scars, lesions, and/or regions of edema, are optionally implemented as appropriately positioned objects, e.g., embedded in an environment of surrounding tissue. Guides and markers are optionally implemented as game objects. |
| Assets | Tissue, probe, guide, and/or other objects and/or their appearances are optionally instantiated from assets that represent available types of objects, their behaviors and/or their appearances. Optionally includes geometrical-type scene data 1225 (e.g. model assets, shapes, and/or meshes), and/or appearance-type scene data 1226, (e.g., image assets, material, shaders, and/or textures). |
| Cameras 1223 | Cameras optionally define simulated flythrough viewpoint(s) of the anatomy traversed by the catheter probe 11, and/or simulated overview viewpoint(s) (showing probe and tissue from a remote viewpoint). Optionally, the position of catheter probe 11 defines one or more camera viewpoints by its position/or orientation. |
| Lighting 1222 | In addition to providing general lighting of the tissue being navigated, lighting 1222 is optionally defined to provide highlighting, e.g., of regions pointed at by probe 11, indications of environmental state by choice of light color, light flashing, etc. Lighting is optionally used to implement MAPs non-locally (that is, a defined light source optionally is defined to illuminate a view of simulated tissue to selectively change its material appearance, while not being part of the material properties of appearance of the simulated tissue as such). |
| Image Assets; Materials, Shaders, and Textures | MAPs that are also material properties of appearance, for example, defining the appearance of tissue as healthy muscle, edematous, fibrotic, heated, cooled, etc. |
| Particle Systems | Type of object optionally used for providing effects such as smoke/steam-like indications of ablation heating, spray, transfer of energy, etc. |
| Collision Detection Service 1213 and Motion Physics Service 1212 | Optionally used for interactions between probe and the geometry of the anatomical environment; optionally including deformation of the probe and/or the anatomy. As implemented by core graphical game engines, the term "physics" generally is limited to physics affecting movement/deformation of game objects such as collision, gravity, or destruction. In some embodiments, simulators 1110 include simulation of other "physics", such as temperature, physiological change, etc. |
| Scripts 1211 | Optionally used for animating and/or showing changes in dynamic features of the environment (lighting, terrain), viewing frame of reference (camera position, orientation, and view angle) and/or game objects: for example, development of lesions, development of edema, heating/cooling effects, and/or injection effects. Optionally, scripts are used to implement dynamic appearance, even though the underlying state representation is constant (e.g., coruscating and/or pulsing effects). |
| User Input 1214 | Optionally comprise inputs reflecting changes in probe position (e.g., output of probe position tracker 1107) for guiding navigation through the scene, and/or determining camera position. Some treatment status data 1102 are optionally interpreted as inputs reflecting operator interaction with the scene. |
| Multiplayer | During a procedure, there are optionally a plurality of different operators working simultaneously with a system according to some embodiments of the current invention. For example, while a primary physician manipulates the probe, one or more additional workers are optionally reviewing the simulated environment to locate next target sites for the probe, evaluate effects of previous ablations, etc. Optionally, there is more than one probe in use at a time, each of which is optionally treated as a different "player" with its own associated camera views and/or interaction capabilities. |

Independently Time-Evolving Probe-Tissue Interactions

In some embodiments of the invention, simulation of probe-tissue interactions includes simulation of cumulative (i.e., developing over time as a result of continued operation of a treatment; for example, heating as a result of transfer of energy over time) and/or tissue effects developing in response to discrete events (e.g., injury response). The flowchart of FIGS. 1B and 1C describe different particular optionally "open loop" cases of the flowchart of FIG. 1A, according to some embodiments of the present disclosure. In FIG. 1B, initial interaction data is received, and the MAPs continue to evolve from simulations which operate substantially independently of further input. A potential advantage of this approach is to allow continuously updated visualization of tissue changes, even when no new sensing data has been obtained to confirm them.

In FIG. 1C, the data received describe what is done (e.g., treatment parameters applied), and simulating is of predicted cumulative effects of the treatment on tissue without necessarily using additional sensing data confirming how the tissue has actually reacted. This is a potential benefit when actual treatment effects are difficult to measure, and/or are difficult to measure at the same time as treatment is occurring.

It is noted that lesioning treatment simulations more particularly described in relation to FIGS. 2A-2E, 3, 4A-4C, 6A-6B optionally make use of all three basic modes of simulation for adjustment and visual presentation of tissue MAPs: simulation based on sensed data, simulation based on predicted independent evolution of physiology in response to lesioning, and simulation based on predicted effects of the operation of device providing a treatment modality suitable for lesioning.

Reference is now made to FIG. 1B, which is a schematic flowchart illustrating the rendering and presentation of a simulated tissue having a material appearance dynamically changing over time as a result of prior interaction of the tissue with a catheter probe, according to some embodiments of the present disclosure.

The flowchart optionally begins after a triggering probe-tissue interaction has occurred which is to be modeled as provoking changes to the scene which continue after the trigger time t0. For example, an input indicating that ablation energy has been delivered triggers the operations of the flowchart.

Optionally, operations of the flowchart of FIG. 1B are implemented by a script 1211. Additionally or alternatively, operations of the flowchart are implemented by a simulator 1110, for example, physiology simulator 1114.

At block 120, in some embodiments, one or more MAPs are set to an initial state and assigned to a simulation function selected to change the MAPs over time according to parameters set from inputs describing the probe-tissue interaction. For example, in some embodiments, physiology simulator 1114 is configured to emulate effects of edema developing post-ablation, based on parameters such as the position, amount of energy delivery, and/or duration of energy delivery causing the ablation. Edema is optionally modeled to develop over the course of several minutes (for example, 2, 5, 10, 15, 20 or another number of minutes). Affected MAPs optionally include, for example, those which can be modified to show increasing "redness" of the tissue with time. Optionally, or alternatively, changes over time affect geometry; for example, to simulate swelling, and/or reduction of muscle tone.

As another example: in some embodiments, MAPs used include indications of electrical impulse transmission (for example, visual indication of impulses using periodic waves of scintillation passing across the simulated material's surface). Optionally, simulations of impulse waves are triggered by measurements of heartbeat and/or pulse phase. In some embodiments, the wave pattern to be simulated is determined at least in part from direct measurements of impulse wave propagation. In some embodiments, the wave pattern is simulated from a generic heart tissue or other tissue model. Optionally, the wave pattern is adapted according to knowledge about tissue state, for example, to indicate regions of weak and/or slow propagation attributed to states of fibrosis, perfusion state, and/or denervation. Optionally, moreover, the degree of impulse transmission is itself modulated in simulations managed by physiology simulator 1114; for example, to reflect transmission effects of treatment activities such as lesioning, tissue cooling, injections, etc.

At block 122, in some embodiments, the current state of the MAPs (optionally including changes to geometry) is rendered to a visual representation of the tissue with which the interaction occurred. In some embodiments, the rendering makes use of 3-D graphics engine, for example as described in relation to display module 1130, and/or in relation to FIG. 12 and Table 1.

At block 124, in some embodiments, the timer is incremented.

At block 126, in some embodiments, a decision is made as to whether the loop is to continue (returning to block 120), or is terminated (stopping the flowchart). Time-evolving MAPs optionally evolve, for example, cyclically (for example, repeating an impulse pattern), transiently (disappearing at the end of a generation cycle, for example, in a simulation of cooling from a heated condition, or re-warming from a cooled condition), and/or to a new steady-state appearance (for example, edema that develops to fully developed state during a period after ablation, and then persists beyond the period during which the tissue is simulated).

It should be understood that sensing feedback is optionally integrated with the flowchart of FIG. 1B to create semi-open/semi-closed loop simulation: periods of open loop simulation producing results (e.g., effect on shape and/or apparent shape) that are periodically verified, guided, and/or corrected according to sensed data. In some embodiments, for example, simulation of developing edema optionally proceeds independently as long as no further sensing data characterizing the edema state is available. However, if edema state is measured at some midpoint of the simulated edema time-course (for example, by use of dielectric measurements), then the simulation is optionally adjusted mid-course to reflect the sensed data. Adjustment is optionally immediate, and/or includes a period of interpolated adjustment (which potentially helps maintain the sense of presence in rendered views of the simulation scene).

Reference is now made to FIG. 1C, which is a schematic flowchart illustrating the iterative rendering and presentation of simulated cumulative treatment effects on a region of tissue, according to some embodiments of the present disclosure.

The flowchart begins; and at block 130, in some embodiments, data describing the operation of a device for administration of a treatment modality are received (that is, treatment operation data). A device for administering a treatment modality optionally comprises any internally navigated therapeutic and/or diagnostic apparatus based, for example, on the introduction of: heat, cold, electrical current, sound radiation, light radiation, and/or substance. In some embodiments, the device for administration of a treatment modality operates by manipulation of tissue; for example, to produce a therapeutic effect, for sampling, and/or to test a response. Examples of treatment modalities are also described in relation to treatment element 8 in the section Receipt of Interaction Data herein.

The data optionally include for example, indications of probe-tissue contact, power delivery, time of power delivery, probe actuation (e.g. of an injection mechanism), and/or other one or more parameters which characterize delivery of treatment.

At block 132, in some embodiments, treatment effects on tissue are modeled, based on the received treatment operation data. In some embodiments, the modeling is performed by one or more of simulators 1110.

At block 134, in some embodiments, MAPs (optionally also changes to geometry) are updated according to simulated effects of treatment on tissue (assuming that the simulation output is not already expressed directly in terms of MAPs).

At block 135, in some embodiments, visual rendering and visual presentation are performed, for example, as described in relation to block 114 of FIG. 1A.

At block 136, in some embodiments, if the treatment is continuing, the loop returns to block 130. Otherwise, the flowchart terminates. Optionally, the visual appearance of the modeled treatment region continues to evolve, for example, according to the method described in relation to FIG. 1B.

It should be understood that sensing feedback is optionally integrated with the flowchart of FIG. 1C to create semi-open or closed-loop simulation: open loop simulation which is periodically verified, guided, and/or corrected according to sensed data.

Visually Rendered Effects of Tissue Ablation

Cross-Sectional Perspective Views of Single-Lesion Progress

Reference is now made to FIGS. 2A-2E, which illustrate a 3-D rendered display for indicating lesioning status to an operator, according to some exemplary embodiments of the present disclosure. FIGS. 2A-2E show a sequence of visual renderings of a single lesion over the course of the operation of an RF ablation probe to create it. This provides an example of how adjusted MAPs can be used to convey to an operator a direct understanding of how use of an ablation probe is affecting target tissue. FIGS. 3 and 4A-4C develop the visualization scenario for the creation of multiple ablations within a procedure.

In appearance, FIGS. 2A-2E comprise images (rendered in some embodiments in the rendering pipeline 1230 of a 3-D graphical game engine 1200) of an RF ablation probe 202 (corresponding, in some embodiments, to catheter probe 11, wherein treatment element 8 is an ablation electrode, and treatment controller 13 operates to supply ablation energy to the RF ablation probe 202) and its position relative to tissue 205 targeted for ablation (part of body tissue region 7). Optionally, the rendering is in color, and/or otherwise using applied MAPs conveying the vital appearance (e.g., properties of roughness, specular reflection, etc.) of the tissue (black and white is shown herein for purposes of illustration). In some embodiments, RF ablation probe 202 is implemented as an object 1224 belonging to scene elements 1220 (FIG. 12). Tissue 205 is optionally implemented as terrain 1221 or an object 1224 belonging to scene elements 1220.

Figure 2A:
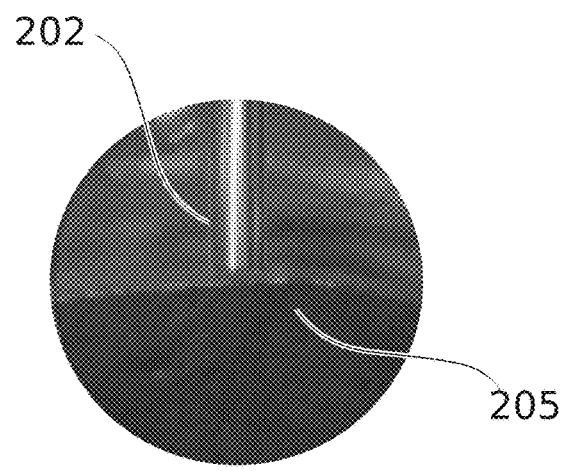
FIGS. 2A-2E illustrate a 3-D rendered display for indicating lesioning status to a user, according to some exemplary embodiments of the present disclosure.

FIG. 2A, in some embodiments, shows the moment of initial contact between probe 202 and tissue 205. Optionally, this view is triggered when contact is sensed by a sensor on the probe, such as a force sensor (an example of an "other sensor" 14) and/or dielectric sensing of contact (e.g., via dielectric property analyzer 22). The triggering, mediated in some embodiments by interaction analyzer 21 (and optionally taking advantage of a collision detection service 1213 of a game engine 1200), is optionally visually implemented as a jump from a wider angle view with the probe out of contact to a close-up of the probe contacting tissue. Optionally, transition from no-contact to contact (or vice versa) is shown by a short bridging animation. In some embodiments, continuous sensing of probe position and/or probe distance to the tissue wall (for example, by a position sensing subsystem comprising sensing electrodes 3, body surface electrodes 5, field generator/measurer 10, and/or position analyzer 20 and/or position tracker 1107) allows any jump in a sensed transition between contact and non-contact to be smoothed out using actual position data.

Figure 2B:
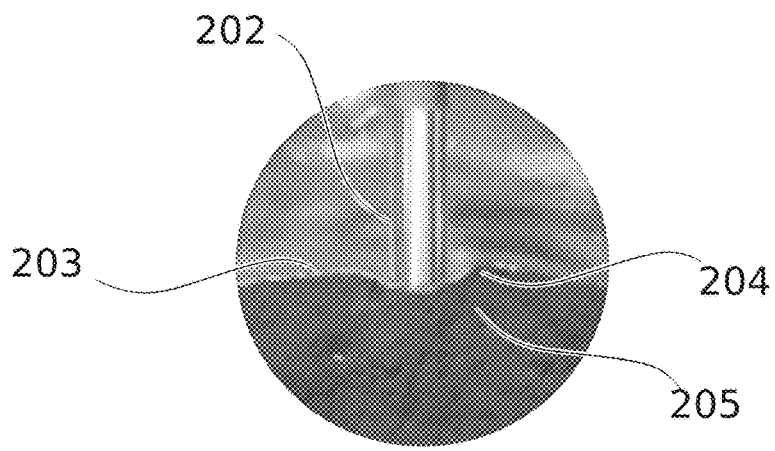
Figure 2C:
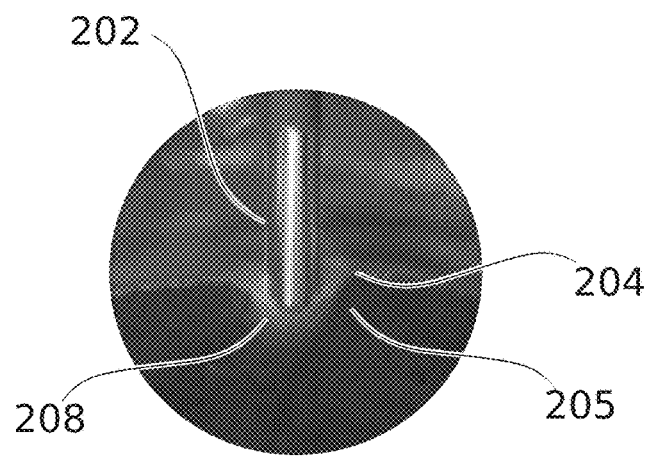
Figure 2D:
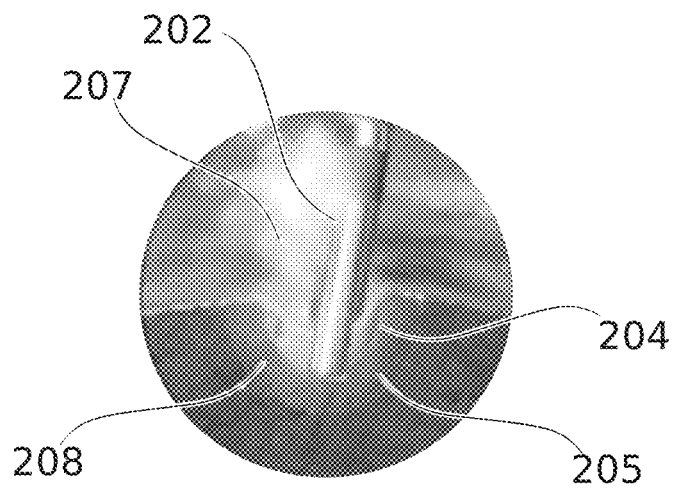
Figure 2E:
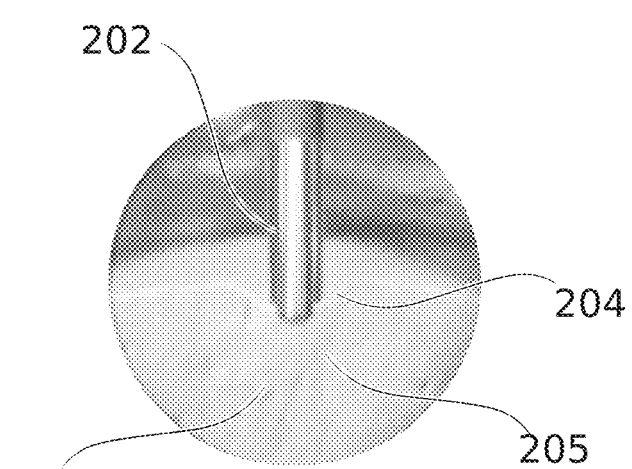

FIG. 2B, in some embodiments, includes a visual indication of increased contact pressure between the tissue 205 and probe 202 comprising an indentation 204. In FIG. 2C and then FIG. 2D, the deeper indentation 204 shows that pressure has been increased still further. Optionally, the material appearance properties modified for this indication correspond to minor modifications of material geometry in response to sensed and/or calculated contact force, the appropriate transformation being calculated, for example, by contact physics simulator 1111 (which may in turn take advantage of motion physics services 1212 and/or collision detection service 1213 of game engine 1200). Although preferably modeled based on sensed contact quality and/or force data, distances of the indentation deformation need not be exactly corresponding to deflection distances in the real tissue. Rather, the visual degree of indentation shown is optionally considered as a proxy indicator for when the probe is out of contact, in poor contact, in a good position to ablate, and/or exerting excessive force on the tissue. Optionally, tissue 205 is shown in cross-section. This has a potential advantage for allowing the indentation size to be clearly seen (as a deflection of the surface boundary 203). Additionally or alternatively, in some embodiments of the invention, transparency effects are applied to allow seeing into a targeted volume of tissue. For example, before ablation begins, a local region of tissue selected by the position of probe 202 is shown with increased transparency. Optionally, as portions of the tissue become lesioned, they are represented in simulated display as more opaque; creating an ablation "island" that directly shows the progress of lesioning. A potential advantage of the transparency approach is to allow representation of lesioning progress from any arbitrary 3-D point of view (simulated viewpoint) including the targeted tissue region.

In FIG. 2C, in some embodiments, there has been a slight increase in sensed contact (shown by increased depth of indentation 204), and ablation by delivery of RF energy to the tissue from probe 202 has begun. A superficial lesioned portion 208 of tissue 205 is now shown, for example, in a lighter shade (in a color display, not shown, lesioned portion 208 is optionally colored a light grey compared to darker red vital tissue). As lesioning proceeds (for example, to the intermediate state indicated in FIG. 2D, and finally to the complete lesion 209 in FIG. 2E), lesioned portion 208 gradually increases in extent and/or degree of MAP change from the pre-lesioned state.

In some embodiments, this progression is based on inputs describing the operation of the device for administering a treatment modality (ablation, in the illustrated example). For example, inputs describing power, duration, and/or contact quality are factored into a simulation (e.g., by an ablation physics simulator 1112) of thermal effects such as described in relation to FIGS. 5A-5B; this thermal simulation is in turn optionally linked to a simulation of resultant physiological states (e.g., physiology simulator 1114), which physiological states are further linked to corresponding characteristic MAPs used in visual rendering for display. Optionally, simulated thermal effects are directly converted to MAPs, for example using a simplifying assumption that physiological state is directly correlated to some local function of temperature (e.g., maximum temperature, maximum temperature integrated over a period of time, etc.). Optionally, changes to MAPs are gradual between "no lesioning" and "fully lesioned", as shown, for example, by the gradient regions near the edges of lesioned portion 208 in FIG. 2D, and of completed lesion 209 in FIG. 2E. In some embodiments, calculated dielectric properties are used as indications of lesion state (e.g., size, transmurality, completeness and/or irreversibility), for example as described in International Patent Application No. PCT/IB2016/052690, the contents of which are incorporated by reference herein in their entirety. In in vitro studies, accuracy of transmurality has been found to be about ±1 mm. In prospective in vivo studies, 100% sensitivity and specificity in predicting lesion transmurality was found, while in humans, at least 90% specificity and sensitivity was found. Specificity is the percentage of actually well-ablated areas that were dielectrically identified as well-ablated; sensitivity is the percentage of actually partially ablated areas that were dielectrically identified as partially ablated.

Additionally or alternatively, the progression during lesioning is based on inputs describing sensed data reflecting one or more treatment effects, for example, measured temperature and/or changes in dielectric properties as tissue begins to break down. In general, probe-based temperature sensing, where available, is limited in resolution and/or depth, so that completely sensing-based adjustment of MAPs is difficult or impossible to obtain. However, the sensed data may nevertheless be used as input to an ablation physics simulator 1112 that extrapolates the lesion state through a 3-D block of tissue. Optionally, the extrapolated state is used as a corrective and/or calibrating input to an ablation physics simulator 1112 operating based primarily on thermal modeling of RF ablation inputs. It should be noted that FIGS. 2A-2E show the tissue 205 in cross-section, which is a potential benefit for conveying to an operator information about achieved lesion parameters such as lesion depth and/or lesion transmurality.

In some embodiments, one or more additional indications of how lesioning is proceeding are provided as part of the rendered image. For example, in FIG. 2D, "steam" 207 is shown arising from the lesion point. Optionally, this is an indication that temperature has reached (and/or is maintained at) a certain threshold. The threshold may be, for example, a threshold at which lesioning occurs, a threshold above which a danger of effects such as steam pop or charring occurs, or another threshold. Different characteristics of the "steam" could be used, for example, conversion to black (or increasingly black) "smoke" in case of increased danger of excessive heating. In some embodiments of the invention, such steam- and/or smoke-like effects are implemented using a particle system facility provided by a graphical game engine.

Lesion Line Progress

Reference is now made to FIG. 3, which represents a display of a screen 400 from a user interface 55 comprising three simultaneously presented visually rendered views 405C, 410C, 415C showing portions of a tissue region 402 (a heart atrial lumen is shown) interacting with a catheter probe 401, according to some embodiments of the present disclosure. In some embodiments, tissue region 402 corresponds to a portion of body tissue region 7, and catheter probe 401 corresponds to catheter probe 11. Simulators 1110, game engine scene elements 1220, and game engine services such as for motion physics service 1212 and collision detection service 1213 are optionally used as also described in relation to elements of FIGS. 2A-2E.

Further reference is made to FIGS. 4A-4C, which each represent three different visually rendered views of tissue region 402 undergoing a sequence of stages of a lesioning procedure, according to some embodiments of the present disclosure.

In some embodiments, the point of view (simulated viewpoint) for a plurality of the views (e.g., views 405C, 410C) is selectable from among a plurality of scene cameras 421 (linked to selection from among cameras 1223 of FIG. 12), to be, for example, from a remote position looking at a wide view of the scene element including the probe ("camera 1", in view 405C); from a "first person" view, e.g. as if holding or riding probe 401 ("camera 4" of view 410C); and/or from another viewpoint, for example, a camera viewpoint above and behind the probe, tracking the probe with the whole probe in view. Optionally, view selection is performed using a control such as view selection button 422. Optionally, views 405C, 410C comprise one or more additional display elements, for example, orientation marker 424 which represents the relative orientation of the left and right atria in the frame of reference of the view.

Optionally, wide-angle view 405C is used for putting interactions of probe 401 with tissue region 402 in broad context—for example, to identify the general region which probe tip 401A is in contact with.

Optionally, the first person view of view 410C allows inspection of the region that probe tip 401A is interacting with, and/or poised to interact with. Shown in view 410C are also planned ablation marks 403, and marks at actual ablations or lesions 408, described further with respect to FIGS. 4A-4C.

In some embodiments of the invention, view 415C comprises a cross-sectional view along a line of planned and/or already created ablation in a region of body tissue (in this case, a path extending along the chain of planned ablations marks 403). Cross sectional view 415C is optionally taken, for example, along a straight line, or along a path curved to pass through a plurality of planned and/or created ablations (said curved path defining a non-planar section extending through a thickness of the body tissue region). In some embodiments, a curved-path cross section is shown as a flattened surface. In the view, surface 412 represents the face exposed by the virtual cross-sectioning. The depth (including degree of transmurality) and lateral extent of lesions 408 can be seen by inspection of surface 412. In some embodiments, the rendering of view 415C is performed as if from a sectioned view of the tissue. In some embodiments, view 415C is rendered as a composite of two images: one of a simulated tissue surface revealed by virtual sectioning, and one of a portion of un-sectioned surface.

In some embodiments, one or more additional indicators are shown in the view. For example, estimated lesion quality indicator 425 comprises an animated gridded hill which increases in height as the predicted properties of a lesion made with the probe in its current position become closer to the planned properties. Go/no-go indicator 426 optionally indicates whether the current probe positioning is adequate to begin lesioning by one or more of the position and/or color of an indicator light 426A.

Turning now to FIGS. 4A-4C, the stages of ablation line creation shown are, respectively, pre-lesioning, during lesioning, and post-lesioning. Wide-angle views 405A, 405B, 405C appear nearly the same throughout, except to indicate the general motion of ablation probe 401 relative to the heart lumen in which it moves.

Views 410A, 410B, 410C show a portion of the planned, and then created, ablation line. Initially, planned ablation marks 403 are optionally shown as marks which replace or superimpose on the material appearance of the heart tissue (as shown, they superimpose). Optionally, planned ablation marks 403 are visually represented as if they are part of the tissue material itself, or alternatively, floating in front of it. In some embodiments of the invention, as ablations are made, MAP changes due to the actual ablation are added to the scene as ablation marks (lesions) 408, for example as described in relation to FIGS. 2A-2E.

In some embodiments, the ablation progress is shown in cross section as well, for example using cross-sectional views 415A, 415B, 415C, and for example as described in relation to FIGS. 2A-2E. View 415B, for example, shows a lesion in progress, including a view of probe 401 in contact with tissue region 402, and ablation 406 spreading within the volume visualized through cross-sectional surface 412. Also shown in view 410B is "steam" 414 that optionally serves to indicate that ablation is actively underway. In some embodiments of the invention, such effects are implemented using a particle system facility provided by a graphical game engine.

Thermal Simulation—Example of Simulation

Figure 5A:
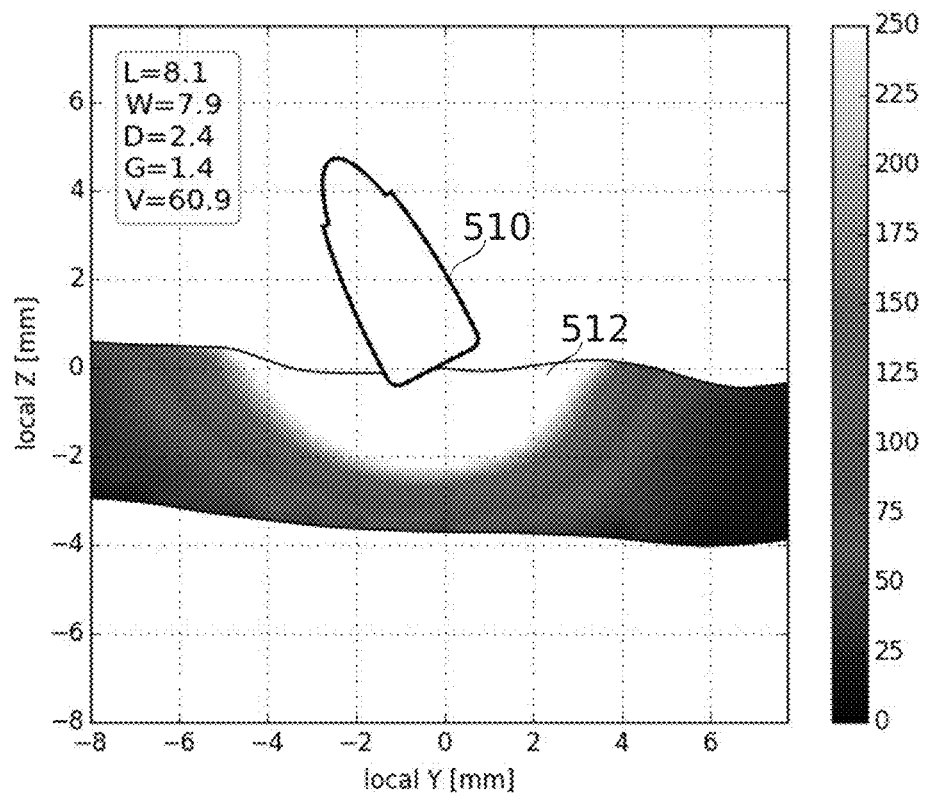
FIG. 5A is a graph depicting the calculated power density loss (PLD) pattern created by an electrode (e.g., RF ablation electrode(s)) in a tissue, according to some embodiments of the present disclosure.

Reference is now made to FIG. 5A, which is a graph depicting the calculated power loss density (PLD) pattern (scaled to arbitrary units) created by an electrode 510 (e.g., RF ablation electrode(s)) in a tissue 512, in accordance with some embodiments of the present invention. The PLD pattern may be calculated using EQU. 1:

$$PLD = \tfrac{1}{2}(\sigma + \omega\varepsilon_0\varepsilon'')|E|^2 = \tfrac{1}{2}\sigma_e|E|^2 \qquad (EQU.\ 1)$$

where:

|E| is the magnitude of electrical field E, generated from electrode 510;

$\omega = 2\pi f$ where f denotes frequency in Hertz (Hz) of the electrical field; and $\sigma_e$ is an effective conductivity of tissue 512, defined as $\sigma + \omega\varepsilon_0\varepsilon_e''$.

In some embodiments, the PLD pattern is used in generating a simulation of temperature effects of RF ablation, for example, as (or as a module of) ablation physics simulator 1112. In general, where PLD is greater, heating is also greater. The simulation of power density loss in tissue and its effect on tissue temperature are also described in International Patent Application No. PCT/IB2016/052688, the contents of which are included by reference herein in their entirety.

In the figure:

D denotes the ablation depth (in mm),

G denotes the gap between the end of the ablated depth and the opposite wall (in mm; generally, D+G represents the wall thickness of the tissue), V denotes the volume of ablated shape in mm³. The top view of an exemplary ablation region may be modeled as an approximately elliptical shape, and the ablated volume as an approximate half-ellipsoid.

The ablation volume may be further denoted by:

L denoting the length in mm of the ablation region (e.g., one axis of the ellipsoid), and W denoting the width in mm of the ablation region (e.g., another axis of the ellipsoid).

Figure 5B:
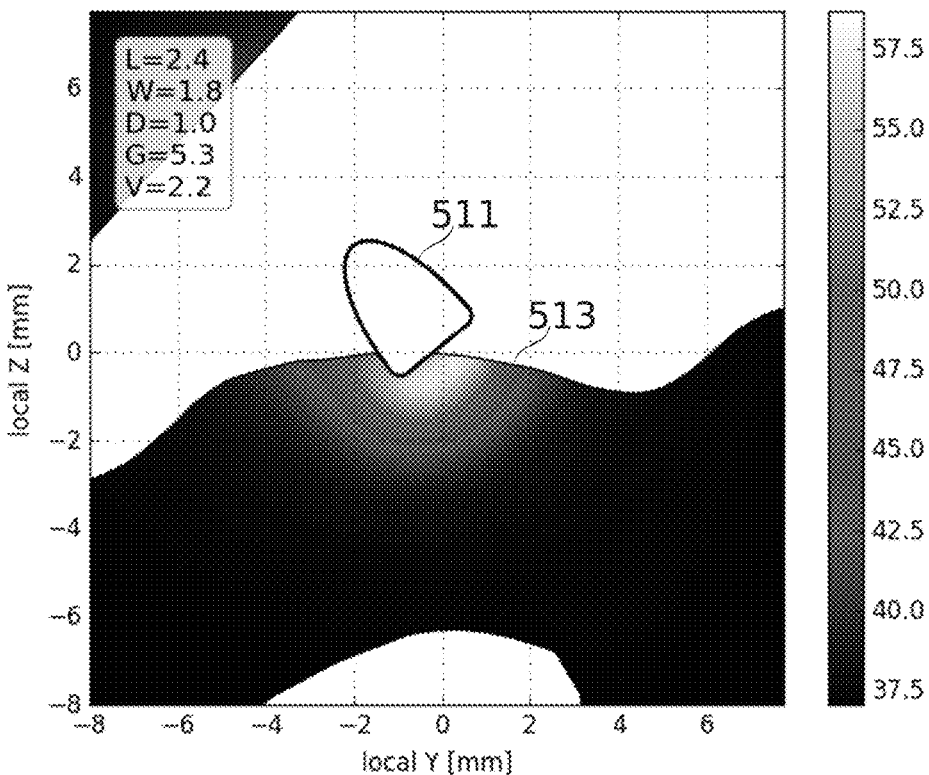
FIG. 5B is a graph depicting the calculated temperature pattern (in degrees Celsius) created by an electrode (e.g., RF ablation electrode(s)) in a tissue, according to some embodiments of the present disclosure.

Reference is now made to FIG. 5B, which is a graph depicting the calculated temperature pattern (in degrees Celsius) created by an electrode 511 (e.g., RF ablation electrode(s)) in a tissue 513, in accordance with some embodiments of the present invention. The temperature pattern may be calculated using EQU. 2. Optionally, the temperature pattern is used in a simulation which provides estimates of changes in tissue state as a function of the delivery of ablation energy over time.

In some embodiments, the temperature pattern is calculated based on an estimation of the rise of temperature, for example according to a continuity equation (e.g., EQU. 2), describing the simple case of electromagnetic heating where the temperature rises at a uniform rate:

$$\frac{\partial T}{\partial t} = \frac{PLD}{\rho c_P} \qquad (EQU.\ 2)$$

where:

$\rho$ denotes the density; and $c_P$ denotes the specific heat.

Optionally, the Gasification Transition (GS) of ablation using cryogenic energy at each possible ablation region is calculated. The GS may be calculated based on the location of each ablation region, the force, the angle of the catheter, and/or other values. Based on the generated simulation, the location, force, angle, and/or other values may be selected to achieve safe GS values, for example, according to a safety requirement.

Contact Simulation—Example of Simulation

Figure 5C:
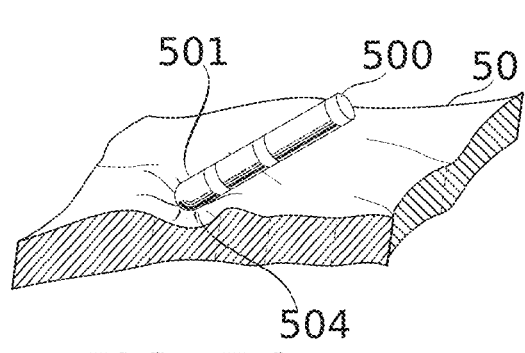
FIGS. 5C-5D schematically represent aspects of geometrical deformation of a tissue region in contact with a catheter probe, according to some embodiments of the present disclosure.
Figure 5D:
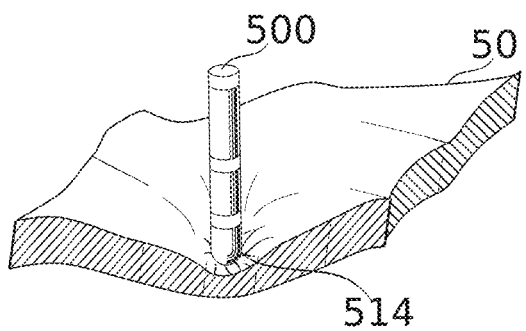

Reference is now made to FIGS. 5C-5D, which schematically represent aspects of geometrical deformation of a rendered tissue region 50 in contact with a catheter probe 500, according to some embodiments of the present disclosure. In some embodiments of the invention, displayed interactions of a probe 500 with a tissue region 50 (a tissue wall, for example) include geometrical deformations of the tissue region to reflect the forces of their interaction.

One type of geometrical deformation is shown in FIG. 5C, which illustrates the use of surface deformation as an indication of contact force or contact quality. The contacting tip 501 of probe 500 is shown denting tissue region 50 at indentation 504 (to an extent and/or depth based on parameters such as contact angle, contact force, and/or dielectrically measured contact quality), but does not substantially change the overall shape of the tissue. This mode of geometrical deformation is a potential advantage for to helping to gauge contact quality before lesioning, and is of particular potential advantage when indentation 504 is shown in cross-section (for example, as discussed in relation to some of FIGS. 2A-4C). This type of geometrical deformation is optionally implemented by deforming the geometrical rendering data itself, and/or by changing one or more material appearance properties assigned to the geometrical rendering data; for example, assigning, for purposes of lighting simulation, a surface orientation which is different than the geometrical rendering data indicate.

In FIG. 5D, a different mode of indentation is shown, wherein the whole tissue region 50 is deformed by probe-tissue interactions around a region of contact 514 by probe

500. Optionally, this is a useful indication to accompany navigation maneuvers where a probe is being pushed to deliberately penetrate a heart wall, for example, transseptal puncture. In some embodiments, the resulting "tenting" is simulated (e.g., by deformation of the geometrical rendering data) based on force measurements made by the catheter itself. Additionally or alternatively, data from a device providing an imaging modality such as intracardial ultrasound are used to selectively morph parts of the cardiac wall in the rendered display. This has the potential advantage of converting a relatively abstract-appearing (cross-sectional, black and white, visually noisy) display of ultrasound-imaged anatomical structures into a solid looking indication of how forces from a catheter are interacting with a heart wall.

Physiological Simulation—Example of Simulation

Figure 6A:
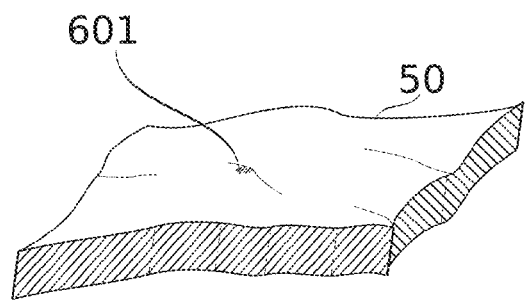
FIGS. 6A-6B schematically represent aspects of geometrical deformation of a tissue region due to an internal change such as edema according to some embodiments of the present disclosure.
Figure 6B:
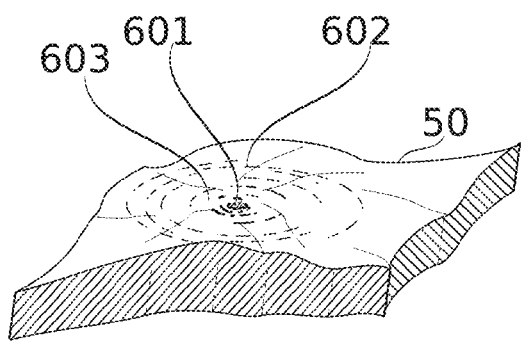

Reference is now made to FIGS. 6A-6B, which schematically represent aspects of geometrical deformation of a tissue region 50 due to an internal change such as edema according to some embodiments of the present disclosure.

In FIG. 6A, lesion region 601 represents a recently formed lesion, for example, an RF ablation lesion. Over the course of a few minutes after RF ablation, tissue potentially reacts with a swelling response. In some embodiments of the invention, the swelling response is simulated (for example, as a function of time according to the method described in relation to FIG. 1B, and/or based on measurements such as dielectric measurements which provide edema data) by one or both of increasing thickness in a region 603 surrounding lesion region 601, and a change in color and/or texture in region 602 (represented by the partial rings in the drawing).

Other Probe and/or Treatment Types

Injection Probes

Figure 6C:
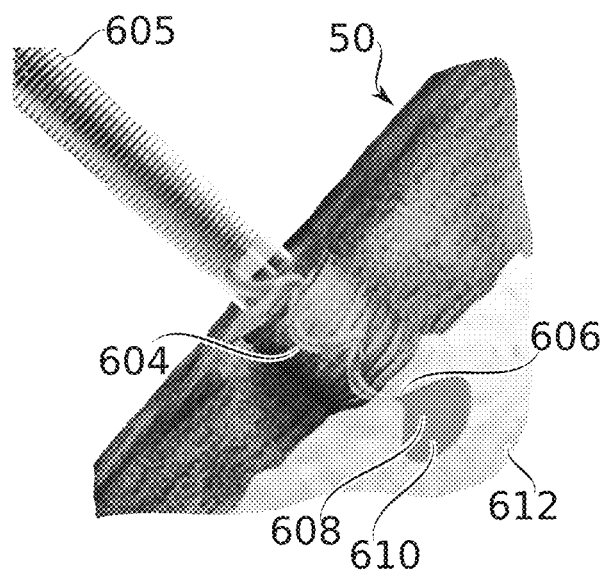
FIG. 6C schematically represent elements of a display showing of a substance being injected to a tissue region, according to some embodiments of the present disclosure.

Reference is now made to FIG. 6C, which schematically represent elements of the display of a material 610 being injected to a tissue region 50, according to some embodiments of the present disclosure.

FIG. 6C is a visually rendered cross-sectional view of a tissue region 50 as it is penetrated by tip 606 of a needle 604 of an injection probe 605 positioned to modulate and/or ablate activity of a ganglion 608 using an injected material 610. In the respect of allowing visualization of the effects of a treatment through a volume of tissue, this cross-section is similar to cross-sections of FIGS. 2A-2E showing the effects of RF ablation. In some embodiments, the distribution of injected material 610 and/or displacement of nearby tissue 612 by injected material 610 is determined by the operations of an injection simulator 1113 that is optionally configured to accept one or parameters including diffusion constants (or other constants governing rate of spread of injected material from an injection site), injection volume, viscosity, projected pharmaceutical effects, etc. and convert them into model adjustments reflected in changes to MAPs and/or geometry. The MAPs are optionally selected to visually trace the modeled distribution of the injected material 610 in tissue 612, and/or to visually indicate actual and/or intuitively "metaphorical" effects on tissue (e.g., a smoothing of the tissue evocative of relaxation).

It should be noted also that FIG. 6C comprises an example of rendering using partial transparency of tissue region 50 in the volume surrounding needle 604. Even when the real tissue being simulated is opaque, it can be a potential advantage to use partial transparency to reveal details which would otherwise be obscured. Transparency is optionally coupled with simulated properties such as refractive index, volume scattering, and/or volume absorption, e.g., to simulate glass, haze, and/or colored transmission media.

Balloon Probes

Reference is now made to FIGS. 7A-7C, which schematically represent dynamically deformable display of balloon 702 of a balloon-equipped catheter probe 700 in contact with tissue region 701 according to some embodiments of the present disclosure.

In some embodiments of the invention, a probe 700 comprises a balloon 702, for example, a balloon 702 mounted to a catheter shaft 703 which is used in cryoablation. In some embodiments of the invention, the inflated or deflated state of the balloon is displayed during manipulation of the probe within cavities of the body (compare FIGS. 7A and 7B for deflated and inflated states, respectively). Optionally, the physics simulation facilities of a graphical game engine are used to represent interactions of the balloon with the tissue surfaces it encounters. For example, a balloon 702 is optionally to be inserted into the root region 701 of a vein in order to create a ring-shaped ablation. It is a potential advantage to visualize deformations of balloon 702, to help verify that the contact region is simultaneously continuous around the root circumference, and not too deeply inserted into the vein root so that the vein itself is at elevated risk for damage. For example, in FIG. 7C, region 707 of the balloon has been flattened while region 705 assumes a relative bulge. The flattened region has the potential to reach deeper into the vein root than the planned procedure calls for.

Laser and Light-Emitting Probes

Reference is now made to FIGS. 8A-8B, which schematically represent the 3-D rendered visual display of light from a laser probe 800 used for lesioning and/or other treatment of a tissue region 50, according to some embodiments of the present disclosure.

In some embodiments, MAPs are applied to a simulated optical medium through which simulated illumination (e.g., from a probe) travels before reaching a camera object representing a simulated viewpoint on a scene. Simulation of optical media and/or material scattering effects is optionally implemented by a 3-D graphical engine rendering pipeline 1230.

In the example shown in FIG. 8A, a simulated source of the light comprises a laser probe 800 (for example, a laser ablation probe). Radiant lines 804 and beam scattering 802 represent simulated scattering of light through an optical medium 820 adjacent to the surface of a tissue region 50. Optionally, the medium is simulated as a transparent fluid (e.g., "air" or "water"—optionally characterized by appropriate parameters of diffraction and scattering, for example); used, for example, in place of an opaque intrabody fluid such as blood. Direct scattering 802 from the laser beam is optionally used to directly indicate the current beam orientation and/or indicate its target. In embodiments where physical contact with a laser probe is made before lesioning or other treatment (and thus, there is no beam distance to represent), a virtually represented beam is optionally still used to assist in targeting.

Radiant lines 804 optionally represent scattering in a transparent medium of probe light previously scattered and/or reflected from the surface of tissue region 50. Apart from potentially adding an element of realism to the scene, radiant lines 804 are optionally modulated to provide indications of beam power, probe contact (which potentially affects efficiency of optical coupling to the tissue), and/or tissue state (for example, ablated tissue scattering property changes optionally also modulate the intensity of secondary scattering visible above the tissue). When no beam scattering 802 is shown, the secondary scattering is optionally used as a main visual indicator of ongoing treatment.

Additionally or alternatively, in some embodiments, one or more MAPs modulate light scattering within a simulated tissue volume. For example, contour lines 808 optionally represent "glow" from within the tissue due to scattering through the volume of tissue region 50 from beam target region 806. Optionally, scattering parameters are modulated as lesioning proceeds, for example, to represent increasing opacity as tissue coagulates.

In some embodiments, a laser treatment for lesioning leaves a lesion mark 810, schematically in FIG. 8A. Though shown dark in the figure, it optionally is represented by any appropriate combination of MAPs, for example as discussed in relation to RF ablation in FIGS. 2A-2E.

Dynamic Shape Probes (Multielectrode Probes)

Reference is now made to FIGS. 9A-9B, which schematically represent dynamically deformable display of a flexible electrode rod 901 of a catheter probe 900 as it interacts with a tissue region 50, according to some embodiments of the present disclosure.

Although the shape of catheter probe 900 is optionally not directly viewed, in some embodiments of the invention, interaction analyzer 21 converts appropriate sensing data to changes in probe shape as electrode rod 901 comes into different degrees of contact with tissue region 50.

In some embodiments, the relative spatial positions of catheter probe 900 and tissue region 50 is available from sensing data 1101 and/or probe position tracker 1107. Additionally or alternatively, sensing data 1101 comprises contact data which indicates regions of electrode rod 901 in contact with tissue. Optionally, contact data also indicates a force and/or quality of tissue-probe contact. Optionally sensors 14 in catheter probe 900 directly sense deformations of electrode rod 901.

As an example, FIGS. 9A and 9B may be considered to be visual renderings of an actual probe 900 being brought into contact with tissue inside a body. Electrodes 904 and 906 in FIG. 9A are measured to be in tissue contact, for example by changes in measured impedance at those electrodes when they contact. Electrode 905 is determined not to be in contact in FIG. 9A, but with increased force, it does contact, as shown in FIG. 9B. Moreover, the orientation and position of base region 902 are optionally determined using measurements from a device providing a position sensing modality (for example, field-sensing electrodes inside base region 902, and/or a device implementing another position sensing technology).

Then, in some embodiments, one or more of simulators 1110 (for example, contact physics simulator 1111) is configured to convert such sensing data into changes to probe state 1123; for example, to bend elements of the probe 900 so that sensed tissue-contacting regions along the probe are also shown in tissue contact in the eventual rendered images. Optionally, the visual rendering of tissue region 50 also reacts to the simulated contact, for example by dimpling (optionally, dimpling to a depth increasing with increased contact force). The simulated probe state 1123 (in particular, the geometry of the probe) is optionally based on constraints and/or simulated forces acting on a motion-physics model of the probe (e.g., customized for the particular probe model) that characterizes its geometry, elasticity, degrees of freedom, etc. This reactive shape modelling of the probe provides a potential advantage by giving feedback to an operator to quickly judge how the probe is interacting with its environment.

General

It is expected that during the life of a patent maturing from this application many relevant catheter probes will be developed; the scope of the term catheter probe is intended to include all such new technologies a priori.

As used herein with reference to quantity or value, the term "about" means "within ±10% of".

The terms "comprises", "comprising", "includes", "including", "having" and their conjugates mean: "including but not limited to".

The term "consisting of" means: "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

The words "example" and "exemplary" are used herein to mean "serving as an example, instance or illustration". Any embodiment described as an "example" or "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features except insofar as such features conflict.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

Throughout this application, embodiments of this invention may be presented with reference to a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as "from 1 to 6" should be considered to have specifically disclosed subranges such as "from 1 to 3", "from 1 to 4", "from 1 to 5", "from 2 to 4", "from 2 to 6", "from 3 to 6", etc.; as well as individual numbers within that range, for example, 1, 2, 3, 4, 5, and 6. This applies regardless of the breadth of the range.

Whenever a numerical range is indicated herein (for example "10-15", "10 to 15", or any pair of numbers linked by these another such range indication), it is meant to include any number (fractional or integral) within the indicated range limits, including the range limits, unless the context clearly dictates otherwise. The phrases "range/ranging/ranges between" a first indicate number and a second indicate number and "range/ranging/ranges from" a first indicate number "to", "up to", "until" or "through" (or another such range-indicating term) a second indicate number are used herein interchangeably and are meant to include the first and second indicated numbers and all the fractional and integral numbers therebetween.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

What is claimed is:

1. A method of visually displaying tissue-probe interactions, the method comprising:
   receiving interaction data indicating contact between an intrabody probe and a body tissue region, wherein the interaction data are associated to positions within the body tissue region;
   deforming geometrical rendering data indicating geometry of the tissue region, based on a change in shape of the body tissue region indicated in the interaction data;
   adjusting data indicating a position of the intrabody probe, based on the interaction data; and
   rendering the deformed geometrical rendering data to a rendered image;
   wherein the rendered image comprises a representation of the intrabody probe in the indicated position; and
   the representation shows the intrabody probe interacting with the deformed geometry of the body tissue region from said indicated position; and
   presenting the rendered image.

2. The method of claim 1, wherein receiving interaction data comprises receiving interaction data indicating contact between an intrabody probe and a surface of a body tissue region, wherein the interaction data are associated to surface locations on said surface of the body tissue region.

3. The method of claim 1, further comprising associating material appearance properties to an extent of the geometrical rendering data, based on the interaction data; and wherein the rendering of the deformed geometrical rendering data uses the associated material appearance properties to produce the rendered image.

4. The method of claim 3, wherein the rendering uses the associated material appearance properties to simulate interactions of tissue represented by the geometrical rendering data, of the tissue indicated as having a change in shape, with light.

5. The method of claim 1, wherein said material properties comprises volumetric material properties.

6. The method of claim 1, wherein the rendered image includes a cross-sectional view of the body tissue region.

7. The method of claim 6, wherein the extent and depth of the deforming represent a local indentation of a thickness of the body tissue region where it is intersected by the cross-sectional view, in response to contact pressure applied to the tissue by the intrabody probe in the indicated position.

8. The method of claim 1, wherein the extent and degree of the deforming simulate stretching of the body tissue region in response to contact pressure applied to the tissue by the intrabody probe in the indicated position.

9. The method of claim 1, wherein the interaction data includes probe-sensed characteristics of tissue in the vicinity of the intrabody probe which modifies the rendering of deformation.

10. The method of claim 1, wherein the interaction data includes operation data indicating activation of the intrabody probe to treat tissue and wherein said rendering reflects both geometrical deformation by the probe and said operational data.

11. The method of claim 1, wherein the interaction data indicate a change of the tissue due to the interaction between the intrabody probe and the body tissue region.

12. The method of claim 1, wherein the receiving comprises receiving interaction data including operation data indicative of use of an ablation device operated using the intrabody probe to ablate in the body tissue region.

13. The method of claim 1, wherein the receiving comprises receiving interaction data measuring a force of contact between the intrabody probe and the body tissue region.

14. The method of claim 1, wherein the interaction data indicate a quality of contact between the intrabody probe and the body tissue region.

15. The method of claim 13, comprising deforming the geometrical rendering data at the region corresponding to the region of contact to an extent based on the measured force of contact.

16. The method of claim 1, wherein the interaction data indicate injection of a substance from the intrabody probe to the body tissue region, which injection affects tissue behavior and/or geometry.

17. The method of claim 1, wherein the geometrical rendering data represent thickness of a tissue in the tissue region, and the associating associates the material appearance properties across an extent of the thickness.

18. The method of claim 1, wherein the receiving, the associating, the rendering, and the presenting are performed for each of a sequence of interactions between the intrabody probe and one or more body tissue regions.

19. The method of claim 1, wherein the representation shows the intrabody probe deformed in shape in response to the indicated contact.

20. The method of claim 19, wherein the rendering is to a rendered image from a simulated viewpoint at least partially based on a determined position of the intrabody probe relative to the tissue region determined from measurements.

21. The method of claim 20, wherein the simulated viewpoint is at least partially based on a determined orientation of the intrabody probe.

22. The method of claim 1, wherein said rendering comprises time-evolving rendering reflecting a physical process other than electrical activity and said rendering also including changes in rendering independent of any probe movement.

23. A system for displaying effects of interactions between an intrabody probe and a body tissue region as images, the system comprising:
computer circuitry configured to:
receive interaction data indicating the interactions, and associated to positions within the body tissue region,
associate, based on the interaction data, material appearance properties to an extent of geometrical rendering data indicating geometry of the tissue region, and
render the geometrical rendering data to a rendered image using the associated material appearance properties; and
a display, configured to present the rendered image.

24. The system of claim 23, wherein the computer circuitry is configured to render the geometrical rendering data using a graphical game engine.

25. The system of claim 23, wherein the interaction data includes sensed positions of the intrabody probe.

26. The system of claim 23, wherein the interaction data includes probe-sensed characteristics of tissue in the vicinity of the probe.

27. The system of claim 23, wherein the interaction data includes treatment status data indicating activation of the intrabody probe to treat tissue.

28. The system of claim 23, wherein the associated material appearance properties are used to simulate interactions of tissue represented by the geometrical rendering data, of the tissue indicated as having a change in shape, with light.

29. The method of claim 1, wherein the rendered image presents the body tissue region as a volume having a superficial surface and a cross-sectional surface.

* * * * *